(12) United States Patent
Sun et al.

(10) Patent No.: US 11,377,400 B1
(45) Date of Patent: Jul. 5, 2022

(54) THREE STAGE CATALYTIC PROCESS FOR PYROLYSIS OIL UPGRADING TO XYLENES

(71) Applicant: Saudi Arabian Oil Company, Dhahran (SA)

(72) Inventors: Miao Sun, Dhahran (SA); Sohel K Shaikh, Dhahran (SA); Ibrahim A. Abba, Dhahran (SA); Zhonglin Zhang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/364,990

(22) Filed: Jul. 1, 2021

(51) Int. Cl.
*C07C 4/06* (2006.01)
*B01J 8/04* (2006.01)
*C07C 2/76* (2006.01)

(52) U.S. Cl.
CPC ............... *C07C 4/06* (2013.01); *B01J 8/0426* (2013.01); *C07C 2/76* (2013.01); *C07C 2529/40* (2013.01)

(58) Field of Classification Search
CPC ......... C07C 4/06; C07C 2/76; C07C 2529/40; B01J 8/0426
See application file for complete search history.

(56) References Cited

U.S. PATENT DOCUMENTS

| | | |
|---|---|---|
| 10,751,709 B1 | 8/2020 | Sun et al. |
| 10,751,710 B1 | 8/2020 | Sun |
| 2009/0050526 A1 | 2/2009 | Chen et al. |
| 2009/0173666 A1 | 7/2009 | Zhou et al. |
| 2015/0014217 A1 | 1/2015 | Smiley et al. |
| 2016/0257889 A1 | 9/2016 | Abdullah et al. |
| 2016/0362618 A1* | 12/2016 | Oprins ................... C10G 69/00 |
| 2017/0050177 A1* | 2/2017 | Greeley ................. B01J 27/049 |
| 2018/0361372 A1 | 12/2018 | Tammana et al. |
| 2019/0016975 A1 | 1/2019 | Coleman et al. |
| 2019/0078027 A1 | 3/2019 | Deimund et al. |

(Continued)

FOREIGN PATENT DOCUMENTS

| | | |
|---|---|---|
| WO | 2013151986 A1 | 10/2013 |
| WO | 2017093056 A1 | 6/2017 |

OTHER PUBLICATIONS

Guerzoni et al. "Catalytic Cracking of a Hydrocarbon Mixture on Combinations of HY and HZSM-5 Zeolites" Chemistry Department, Journal of Catalysis 139, 289-303 (1993), 15 pgs.

(Continued)

*Primary Examiner* — Thuan D Dang
(74) *Attorney, Agent, or Firm* — Dinsmore & Shohl, LLP

(57) ABSTRACT

A method for upgrading pyrolysis oil includes contacting a pyrolysis oil feed with hydrogen in the presence of a mixed metal oxide catalyst in a slurry reactor to produce an intermediate stream comprising light aromatic compounds comprising mono-aromatic compounds, di-aromatic compounds, or both, passing the intermediate stream to a hydrocracking reactor, contacting the intermediate stream with hydrogen in the presence of a hydrocracking catalyst in a hydrocracking reactor to produce a hydrocracking effluent comprising aromatic compounds having six to nine carbon atoms, passing the hydrocracking effluent to a transalkylation reactor, and contacting the hydrocracking effluent with hydrogen in the presence of a transalkylation catalyst in the transalkylation reactor to produce a transalkylation effluent comprising xylenes.

17 Claims, 4 Drawing Sheets

(56) References Cited

U.S. PATENT DOCUMENTS

| | | |
|---|---|---|
| 2019/0078029 A1 | 3/2019 | Johnson et al. |
| 2019/0203130 A1 | 7/2019 | Mukherjee |
| 2021/0001321 A1 | 1/2021 | Sun |
| 2021/0009907 A1 | 1/2021 | Frecon et al. |

OTHER PUBLICATIONS

Jimenez-Cruz et al. "Molecular size evaluation of linear and branched paraffins from the gasoline pool by DFT quantum chemical calculations" Science Direct, Fuel 83 (2004) 2183-2188, 7 pgs.

Kim et al. "Novel Ni2P/zeolite catalysts for naphthalene hydrocracking to BTX" Catalysis Communications 45 (2014) 133-138, 6 pgs.

Kim et al. "Morphology effect of b-zeolite supports for Ni2P catalysts on the hydrocracking of polycyclic aromatic hydrocarbons to benzene, toluene, and xylene" Journal of Catalysis 351 (2017) 67-78, 12 pgs.

Kondoh et al., "Catalytic cracking of heavy oil over TiO2—ZrO2 catalysts under superheated steam conditions", Fuel, vol. 167, pp. 288-294, 2016.

Kondoh et al., "Effects of H2O Addition on Oil Sand Bitumen Cracking Using a CeO2—ZrO2—Al2O3—FeOx Catalyst", Energy & Fuels, vol. 30, pp. 10358-10364, 2016.

Kondoh et al., "Upgrading of oil sand bitumen over an iron oxide catalyst using sub- and super-critical water", Fuel Processing Technology, vol. 145, pp. 96-101, 2016.

Lapinas et al. "Catalytic Hydrogenation and Hydrocracking of Fluorene: Reaction Pathways, Kinetics, and Mechanisms" Ind. Eng. Chem. Res. 1991, 30, 42-50, 9 pgs.

Leite et al. "Hydrocracking of phenanthrene over bifunctional Pt catalysts" Catalysis Today 65 (2001) 241-247, 7 pgs.

Lemberton et al. "Catalytic hydroconversion of simulated coal tars" Applied Catalysis A: General, 79 (1991) 115-126, 12 pgs.

Matsui et al. "Explanation of Product Distribution of Hydrocracking Reaction of Aromatic Hydrocarbons with Nickel-Loaded Zeolites Based on CAMD Study on Interaction between Zeolites and Substrates" Energy & Fuels (1995) 9, 435-438, 4 pgs.

Park et al. "Hydro-conversion of 1-methyl naphthalene into (alkyl)benzenes over alumina-coated USY zeolite-supported NiMoS catalysts" Fuel 90 (2011) 182-189, 8 pgs.

Park et al. "Mild hydrocracking of 1-methyl naphthalene (1-MN) over alumina modified zeolite" Journal of Industrial and Engineering Chemistry 19 (2013) 627-632, 6 pgs.

Tailleur et al. The effect of aromatics on paraffin mild hydrocracking reactions (WNiPd/CeY—Al2O3), Fuel Processing Technology 89 (2008) 808-818, 11 pgs.

U.S. Office Action dated Feb. 23, 2022 pertaining to U.S. Appl. No. 17/365,008, filed Jul. 1, 2021, 19 pages.

\* cited by examiner

THREE STAGE CATALYTIC PROCESS FOR PYROLYSIS OIL UPGRADING TO XYLENES

BACKGROUND

Field

The present disclosure generally relates to methods and systems for upgrading pyrolysis oil, more specifically, methods and systems for upgrading pyrolysis oil to xylenes using a three stage catalytic process.

Technical Background

Crude oil can be converted to valuable chemical intermediates and products through one or more hydrotreating processes. The hydrotreating processes can include steam cracking, in which larger hydrocarbons in the crude oil are cracked to form smaller hydrocarbons. Steam cracking units produce a bottom stream, which is referred to as pyrolysis oil. The pyrolysis oil may include an increased concentration of aromatic compounds compared to the crude oil feedstock. In many crude oil processing facilities, this pyrolysis oil is burned as fuel. However, the aromatic compounds in the pyrolysis oil can be converted to greater value chemical products and intermediates, which can be used as building blocks in chemical synthesis processes. For example, aromatic compounds from the pyrolysis oil can be converted into xylenes, which can be the initial building blocks for producing terephthalic acid, which can then be used to produce polyesters. The aromatic compounds in the pyrolysis oil can be upgraded to many other greater value aromatic products and intermediates. The market demand for these greater value aromatic compounds continues to grow.

SUMMARY

Multi-ring aromatic compounds in the pyrolysis oil can be converted to light aromatic compounds, which can include benzene, toluene, ethylbenzene, xylenes, other aromatic compounds, or combinations of these by various reactions, such as, but not limited to hydrogenation, ring opening, disproportionation, dealkylation, transalkylation, cracking, or aromatic cracking. In general, these conventional processes convert a portion of the multi-ring aromatic compounds in the pyrolysis oil to light aromatic compounds in a single step. However, the single step process may be complex and insufficient to meet the increasing demand for xylenes. Further, these conventional processes may be difficult to accomplish without employing severe conditions.

Accordingly, ongoing needs exist for improved systems and methods for upgrading pyrolysis oils to produce light aromatic compounds to increase the yield of xylenes using mild conditions. Embodiments of the present disclosure meet this need by providing a three stage catalytic process, which may upgrade pyrolysis oils to xylenes in a single process by using a slurry reactor, a hydrocracking reactor, and a transalkylation reactor in series. The slurry reactor may include a mixed metal oxide catalyst and may be operable to convert at least a portion of multi-ring compounds in the pyrolysis oil to the light aromatic compounds, such as mono-aromatic compounds, di-aromatic compounds, or both. The hydrocracking reactor may include a hydrocracking catalyst and may be operable to convert at least a portion of the light aromatic compounds to aromatic compounds having six to nine carbon atoms. The transalkylation reactor may include a transalkylation catalyst and may be operable to convert at least a portion of the aromatic compounds having 6 to 9 carbon atoms to xylenes. The methods and systems may convert a portion of the multi-ring aromatic compounds in the pyrolysis oil to xylenes in a three stage catalytic process, without conducting a subsequent chemical reaction step. The methods and systems may also produce greater yields of xylenes from upgrading pyrolysis under mild conditions compared to upgrading pyrolysis oil in a single step.

According to one or more aspects of the present disclosure, a method for upgrading pyrolysis oil may include contacting the pyrolysis oil feed with hydrogen in the presence of a mixed metal oxide catalyst in a slurry reactor to produce light aromatic compounds. The pyrolysis oil feed may comprise multi-ring aromatic compounds comprising greater than or equal to sixteen carbon atoms, and the mixed metal oxide catalyst comprises a plurality of catalyst particles and each of the plurality of catalyst particles comprises a plurality of different metal oxides. The method may further include contacting the pyrolysis oil feed with hydrogen in the presence of the mixed metal oxide catalyst in the slurry reactor to convert at least a portion of the multi-ring aromatic compounds in the pyrolysis oil feed to the light aromatic compounds comprising mono-aromatic compounds, di-aromatic compounds, or both. The method may further include passing an intermediate stream comprising the light aromatic compounds from the slurry reactor to a hydrocracking reactor, and contacting the intermediate stream with hydrogen in the presence of a hydrocracking catalyst in the hydrocracking reactor. The contacting may cause at least a portion of the light aromatic compounds in the intermediate stream to undergo hydrocracking to produce a hydrocracking effluent comprising aromatic compounds having six to nine carbon atoms. The method may further include passing the hydrocracking effluent from the hydrocracking reactor to a transalkylation reactor, and contacting the hydrocracking effluent with hydrogen in the presence of a transalkylation catalyst in the transalkylation reactor. The contacting may cause at least a portion of the aromatic compounds in the hydrocracking effluent to undergo transalkylation to produce a transalkylation effluent comprising xylenes.

According to one or more other aspects of the present disclosure, a system for upgrading pyrolysis oil may include a slurry reactor comprising a mixed metal oxide catalyst comprising a plurality of catalyst particles. Each of the plurality of catalyst particles may comprise a plurality of different metal oxides. The slurry reactor may be operable to contact the pyrolysis oil feed with hydrogen in the presence of the mixed metal oxide catalyst to produce light aromatic compounds comprising mono-aromatic compounds, di-aromatic compounds, or both. The system may further include a slurry reactor effluent separator disposed downstream of the slurry reactor and operable to separate the slurry reactor effluent to produce a used mixed metal oxide catalyst and an intermediate stream comprising the light aromatic compounds. The system may further include a hydrocracking reactor disposed downstream of the slurry reactor effluent separator and comprising a hydrocracking catalyst. The hydrocracking reactor may be operable to contact the intermediate stream with hydrogen in the presence of the hydrocracking catalyst to produce a hydrocracking effluent comprising aromatic compounds having six to nine carbon atoms. The system may further include a transalkylation reactor disposed downstream of the hydrocracking reactor and comprising a transalkylation catalyst. The transalkylation reactor may be operable to contact the hydrocracking effluent with hydrogen in the presence of the transalkylation catalyst to produce a transalkylation effluent comprising xylenes.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
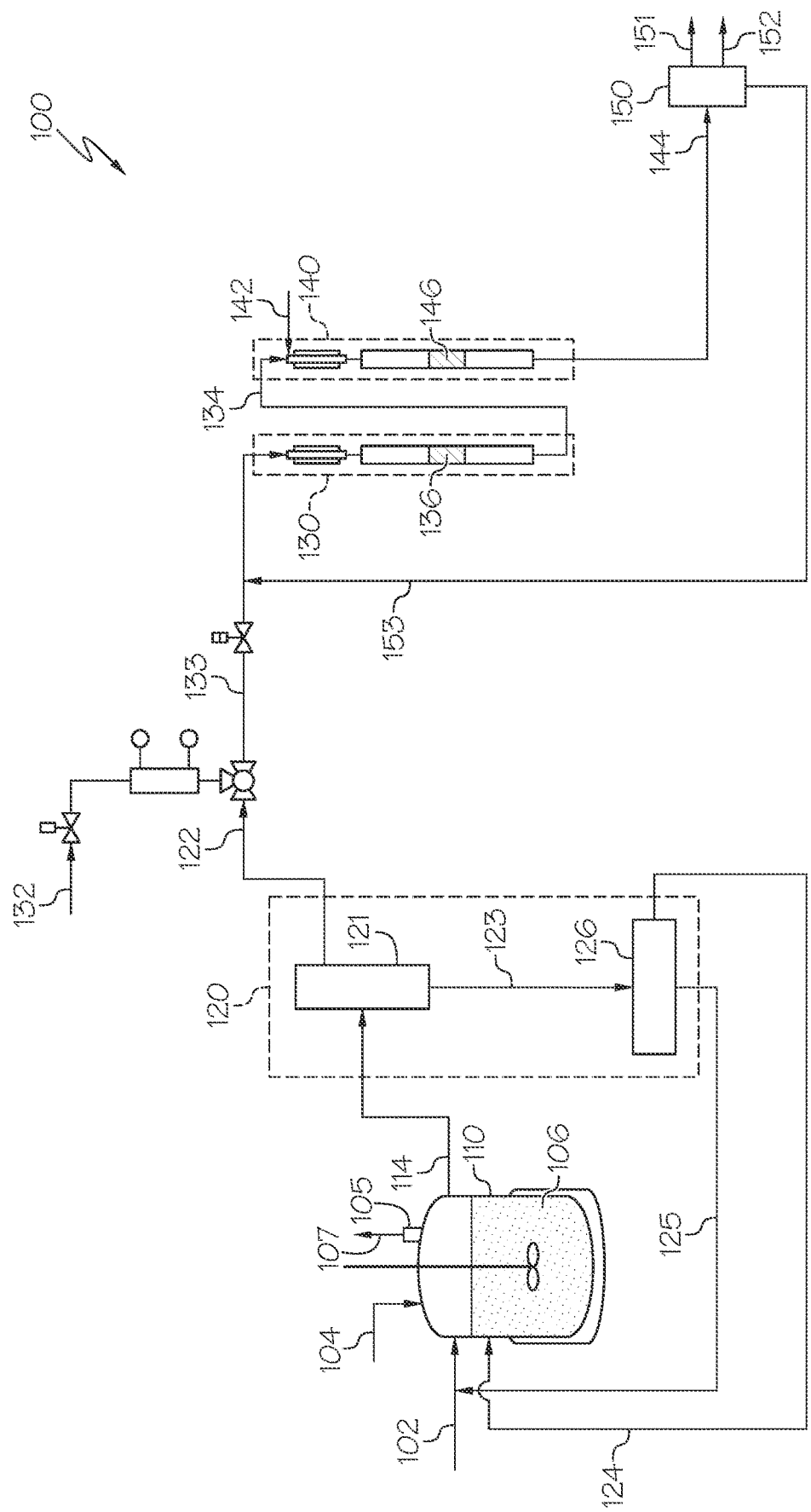
FIG. 1 schematically depicts a generalized flow diagram of a system for upgrading a pyrolysis oil, according to one or more embodiments shown and described in this disclosure.

For the purpose of describing the simplified schematic illustration and description of FIG. 1, the numerous valves, temperature sensors, electronic controllers, and the like that may be employed and well known to those of ordinary skill in the art of certain chemical processing operations are not included. Further, accompanying components that are often included in chemical processing operations, such as, for example, air supplies, heat exchangers, surge tanks, catalyst hoppers, or other related systems are not depicted. It would be known that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines that may serve to transfer process steams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows that do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagram of FIG. 1. Mixing or combining may also include mixing by directly introducing both streams into a like reactor, separation device, or other system component. For example, it should be understood that when two streams are depicted as being combined directly prior to entering a separator or reactor, that in some embodiments, the streams could equivalently be introduced into the separator or reactor and be mixed in the reactor.

Reference will now be made in greater detail to various embodiments of the present disclosure, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to methods and systems for upgrading pyrolysis oil. Referring now to FIG. 1, one embodiment of a system 100 of the present disclosure for upgrading a pyrolysis oil feed 102 is schematically depicted. The systems 100 for upgrading a pyrolysis oil feed 102 may comprise a slurry reactor 110, a slurry reactor effluent separator 120 disposed downstream of the slurry reactor 110, a hydrocracking reactor 130 disposed downstream of the slurry reactor effluent separator 120, and a transalkylation reactor 140 downstream of the hydrocracking reactor 130. The slurry reactor 110 may include a mixed metal oxide catalyst 106 comprising a plurality of catalyst particles and each of the plurality of catalyst particles comprises a plurality of different metal oxides, such as at least a first metal oxide and a second metal oxide. The slurry reactor 110 may be operable to contact the pyrolysis oil feed 102 with hydrogen 104 in the presence of the mixed metal oxide catalyst 106 to produce a slurry reactor effluent 114. The slurry reactor effluent separator 120 disposed downstream of the slurry reactor 110 may be operable to separate the slurry reactor effluent 114 to produce a used mixed metal oxide catalyst 124 and an intermediate stream 122 comprising light aromatic compounds. The hydrocracking reactor 130 may be disposed downstream of the slurry reactor effluent separator 120. The hydrocracking reactor 130 may include the hydrocracking catalyst 136. The hydrocracking reactor 130 may be operable to contact the intermediate stream 122 with hydrogen 132 in the presence of the hydrocracking catalyst 136 to produce a hydrocracking effluent 134. The transalkylation reactor 140 may be disposed downstream of the hydrocracking reactor 130. The transalkylation reactor 140 may include a transalkylation catalyst 146. The transalkylation reactor 140 may be operable to contact the hydrocracking effluent 134 with hydrogen 142 in the presence of the transalkylation catalyst 134 to produce a transalkylation effluent 144 comprising xylenes.

The present disclosure is also directed to methods for upgrading pyrolysis oil feed 102. In particular, the methods may comprise contacting the pyrolysis oil feed 102 with hydrogen 104 in the presence of a mixed metal oxide catalyst 106 in the slurry reactor 110 to produce light aromatic compounds. The contacting the pyrolysis oil feed 102 with hydrogen 104 in the presence of the mixed metal oxide catalyst 104 in the slurry reactor 110 may convert at least a portion of the multi-ring aromatic compounds in the pyrolysis oil feed 102 to the light aromatic compounds comprising mono-aromatic compounds, di-aromatic compounds, or both. The methods may further comprise passing an intermediate stream 122 comprising the light aromatic compounds from the slurry reactor 110 to the hydrocracking reactor 130, and contacting the intermediate stream 122 with hydrogen 132 in the presence of the hydrocracking catalyst 136. The contacting the intermediate stream 122 with hydrogen 132 in the presence of the hydrocracking catalyst 136 may cause at least a portion of the light aromatic compounds in the intermediate stream 122 to undergo hydrocracking to produce the hydrocracking effluent 114 comprising aromatic compounds having six to nine carbon atoms. The methods may further comprise passing the hydrocracking effluent 134 from the hydrocracking reactor 130 to the transalkylation reactor 140. The methods may further comprise contacting the hydrocracking effluent 134 with hydrogen 142 in the presence of the transalkylation catalyst 146 in the transalkylation reactor 140. The contacting the hydrocracking effluent 134 with hydrogen 142 in the presence of the transalkylation catalyst 146 may cause at least a portion of the aromatic compounds in the hydrocracking effluent 134 to undergo transalkylation to produce the transalkylation effluent 144 comprising xylenes.

The various methods and systems of the present disclosure for upgrading pyrolysis oil may increase the yields of xylenes through a three stage catalytic process under mild conditions. Traditionally, pyrolysis oil has not been able to be upgraded to xylenes in a single processing step under mild conditions. Further, existing single step processes can be complex and can be insufficient to meet the demand of xylenes.

In the methods and systems of the present disclosure, the pyrolysis oil may be contacted with hydrogen in the presence of the mixed metal oxide catalyst to covert multi-ring aromatic compounds in the pyrolysis oil to light aromatic compounds comprising mono-aromatic compounds, di-aromatic compounds, or both and then the light aromatic compounds may be contacted with hydrogen in the presence of the hydrocracking catalyst to undergo hydrocracking to produce aromatic compounds having six to nine carbon atoms. The aromatic compounds having six to nine carbon atoms may be contacted with hydrogen in the presence of the transalkylation to undergo transalkylation to produce xylenes. These three stage catalytic processes may increase the yields of xylenes through a single process by using a slurry reactor, a hydrocracking reactor, and a transalkylation reactor in series under mild conditions.

As used in this disclosure, a "catalyst" may refer to any substance that increases the rate of a specific chemical reaction. Catalysts and catalyst components described in this disclosure may be utilized to promote various reactions, such as, but not limited to selective hydrogenation, ring opening, disproportionation, dealkylation, hydrodealkylation, transalkylation, cracking, aromatic cracking, other chemical reactions, or combinations of these.

As used in this disclosure, "cracking" may refer to a chemical reaction where a molecule having carbon-carbon bonds is broken into more than one molecule by the breaking of one or more of the carbon-carbon bonds; where a compound including a cyclic moiety, such as an aromatic, is converted to a compound that does not include a cyclic moiety; or where a molecule having carbon-carbon double bonds are reduced to carbon-carbon single bonds. Some catalysts may have multiple forms of catalytic activity, and calling a catalyst by one particular function does not render that catalyst incapable of being catalytically active for other functionality.

As used in this disclosure, the term "aromatic compounds" may refer to one or more compounds having one or more aromatic ring structures. The term "light aromatic compounds" may refer to one or more compounds having an aromatic ring, with or without substitution, and from six to nine carbon atoms. The term "BTEX" may refer to any combination of benzene, toluene, ethylbenzene, para-xylene, meta-xylene, and ortho-xylene.

As used in this disclosure, the term "xylenes," when used without a designation of the isomer, such as without one of the prefixes para, meta, or ortho, may refer to one or more of meta-xylene, ortho-xylene, para-xylene, and mixtures of these xylene isomers.

As used in this disclosure, the term "outer surfaces" may refer to surfaces at the outer periphery of a catalyst or catalyst support, such as the hierarchical mesoporous zeolite support.

As used in this disclosure, the term "pore surfaces" may refer to the inner surfaces of pores in a catalyst or catalyst support, where the pores include at least the pores in fluid communication with the outer surfaces of the catalyst or catalyst support and are accessible to reactants.

As used in this disclosure, the "average pore size" of a catalyst or catalyst support may refer to the average pore size determined by Barrett-Joyner-Halenda (BJH) analysis. BJH analysis measures the amount of a gas (argon) that detaches from a material, such as the hierarchical mesoporous zeolite support, at 87 Kelvin over a range of pressures. Using the Kelvin equation, the amount of argon adsorbate removed from the pores of the material and the relative pressure of the system can be used to calculate the average pore size of the material.

As used throughout the present disclosure, the terms "upstream" and "downstream" may refer to the relative positioning of unit operations with respect to the direction of flow of the process streams. A first unit operation of a system may be considered "upstream" of a second unit operation if process streams flowing through the system encounter the first unit operation before encountering the second unit operation. Likewise, a second unit operation may be considered "downstream" of the first unit operation if the process streams flowing through the system encounter the first unit operation before encountering the second unit operation.

As used in the present disclosure, passing a stream or effluent from one unit "directly" to another unit may refer to passing the stream or effluent from the first unit to the second unit without passing the stream or effluent through an intervening reaction system or separation system that substantially changes the composition of the stream or effluent. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent. Combining two streams or effluents together upstream of a process unit also is not considered to comprise an intervening system that changes the composition of one or both of the streams or effluents being combined. Simply dividing a stream into two streams having the same composition is also not considered to comprise an intervening system that changes the composition of the stream.

As used in this disclosure, a "separator" refers to any separation device that at least partially separates one or more chemicals that are mixed in a process stream from one another. For example, a separator may selectively separate differing chemical species from one another, forming one or more chemical fractions. Examples of separators include, without limitation, distillation columns, flash drums, knock-out drums, knock-out pots, centrifuges, filtration devices, traps, scrubbers, expansion devices, membranes, solvent extraction devices, and the like. It should be understood that separation processes described in this disclosure may not completely separate all of one chemical consistent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separator and be divided or separated into two or more process streams of desired composition. Further, in some separation processes, a "light fraction" and a "heavy fraction" may separately exit the separator. In general, the light fraction stream has an average boiling point less than the heavy fraction stream. It should be additionally understood that where only one separator is depicted in a figure or described, two or more separators may be employed to carry out the identical or substantially identical separation, unless otherwise stated. For example, where a distillation column with multiple outlets is described, it is contemplated that several separators arranged in series may equally separate the feed stream and such embodiments are within the scope of the presently described embodiments.

As used in this disclosure, the term "effluent" may refer to a stream that is passed out of a reactor, a reaction zone, or a separator following a particular reaction or separation process. Generally, an effluent has a different composition than the stream that entered the separator, reactor, or reaction zone. It should be understood that when an effluent is passed to another system unit, only a portion of that system stream may be passed. For example, a slip stream (having the same composition) may carry some of the effluent away, meaning that only a portion of the effluent may enter the downstream system unit. The term "reaction effluent" may more particularly be used to refer to a stream that is passed out of a reactor or reaction zone.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "hydrogen stream" passing to a first system component or from a first system component to a second system component should be understood to equivalently disclose "hydrogen" passing to the first system component or passing from a first system component to a second system component.

Referring again to FIG. 1, a system 100 for upgrading a pyrolysis oil feed 102 is schematically depicted. The system 100 for upgrading a pyrolysis oil feed 102 may include a slurry reactor 110, a slurry reactor effluent separator 120 downstream of the slurry reactor 110, a hydrocracking reactor 130 downstream of the slurry reactor effluent separator 120, a transalkylation reactor 140 downstream of the hydrocracking reactor 130, and a transalkylation effluent separator 150 downstream of the transalkylation reactor 140. The slurry reactor 110 may include one or a plurality of slurry phase reactors and may be operable to contact the pyrolysis oil feed 102 with hydrogen 104 in the presence of a catalyst to produce a slurry reactor effluent 114. The catalyst is the mixed metal oxide catalyst 106 of the present disclosure. The slurry reactor effluent 114 may be passed to the slurry reactor effluent separator 120, which may include one or a plurality of separation processes or unit operations. The slurry reactor effluent separator 120 may be operable to separate the slurry reactor effluent 114 to produce an intermediate stream 122 and a used mixed metal oxide catalyst 124. The intermediate stream 122 may comprise light aromatic compounds. In particular, the intermediate stream 122 may comprise mono-aromatic compounds, di-aromatic compounds, or both. The hydrocracking reactor 130 may be operable to contact the intermediate stream 122 with hydrogen 132 in the presence of the hydrocracking catalyst 136 to produce a hydrocracking effluent 134. The transalkylation reactor 140 may be operable to contact the hydrocracking effluent 134 with hydrogen 142 in the presence of the transalkylation catalyst 146 to produce a transalkylation effluent 144. The transalkylation effluent separator 150 may be operable to separate the transalkylation effluent 144 to produce a light gas effluent 151, a xylene-containing effluent 152 comprising the xylenes, and a bottom stream 153.

Figure 2:
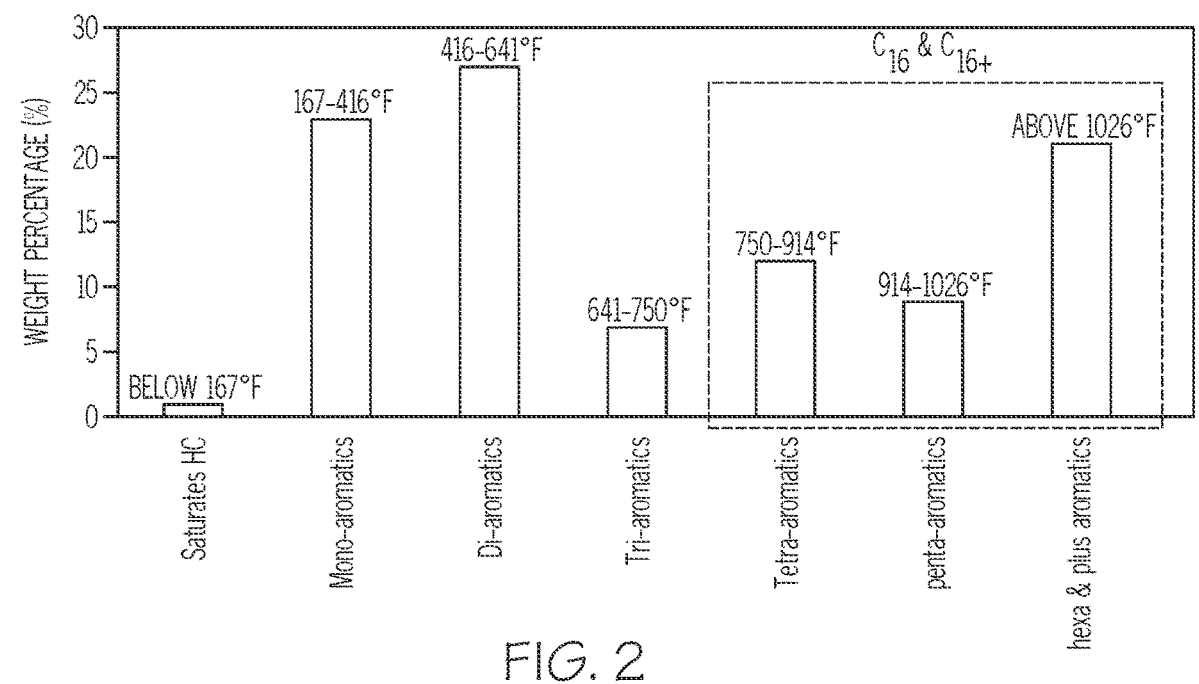
FIG. 2 graphically depicts weight percentage (y-axis) of various constituents (x-axis) present in a pyrolysis oil, according to one or more embodiments shown and described in this disclosure.

The pyrolysis oil feed 102 may include a pyrolysis oil. In embodiments, the pyrolysis oil feed 102 may also include a diluent. The pyrolysis oil may be a stream from a hydrocarbon processing facility that is rich in aromatic compounds, such as multi-ring aromatic compounds. In embodiments, the pyrolysis oil of the pyrolysis oil feed 102 may be a bottom stream from a steam cracking process. As used in the present disclosure, "bottom stream" may refer to a residuum or a fraction of the feed (such as the feed to a steam cracking process) including the least volatile constituents that have not been separately captured as condensed vapor. The pyrolysis oil of the pyrolysis oil feed 102 may include mono-aromatic compounds and multi-ring aromatic compounds. Multi-ring aromatic compounds may include aromatic compounds including 2, 3, 4, 5, 6, 7, 8, or more than 8 aromatic ring structures. Multi-ring aromatic compounds may include aromatic compounds including greater than or equal to sixteen carbon atoms. The pyrolysis oil of the pyrolysis oil feed 102 may also include other components, such as but not limited to saturated hydrocarbons. Referring to FIG. 2, the composition of a typical pyrolysis oil that can be used in the pyrolysis oil feed 102 is graphically depicted. The pyrolysis oil depicted in FIG. 2 is a pyrolysis oil produced from steam cracking crude oil from Saudi Arabia. As shown in FIG. 2, the pyrolysis oil of the pyrolysis oil feed 102 may include mono-aromatics, di-aromatics, tri-aromatics, tetra-aromatics, penta-aromatics, and aromatic compounds having 6 or more aromatic rings (hexa & plus aromatics in FIG. 2). The pyrolysis oil of the pyrolysis oil feed 102 may include elevated concentrations of di-aromatic compounds and aromatic compounds having greater than or equal to 6 aromatic rings, as indicated by FIG. 2. In embodiments, the pyrolysis oil feed 102 that is rich in multi-ring aromatic compounds may include greater than or equal to 50 wt. % multi-ring aromatic compounds, such as greater than or equal to 60 wt. %, greater than or equal to 65 wt. %, greater than or equal to 70 wt. %, greater than or equal to 75 wt. %, or even greater than or equal to 80 wt. % multi-ring aromatic compounds based on a unit weight of the pyrolysis oil in the pyrolysis oil feed 102.

A significant portion of the pyrolysis oil in the pyrolysis oil feed 102 may be multi-ring aromatic compounds having greater than 16 carbon atoms, four or more aromatic rings, or both. The pyrolysis oil of the pyrolysis oil feed 102 may include greater than or equal to 30 wt. % multi-ring aromatic compounds having greater than or equal to sixteen carbon atoms, such as greater than or equal to 35 wt. %, greater than or equal to 40 wt. %, or even greater than or equal to 45 wt. % multi-ring aromatic compounds having greater than or equal to sixteen carbon atoms, based on the unit weight of the pyrolysis oil in the pyrolysis oil feed 102. The pyrolysis oil of the pyrolysis oil feed 102 may include greater than or equal to 30 wt. % multi-ring aromatic compounds having a boiling point temperature greater than or equal to 750 degrees Fahrenheit (° F.) (399° C.), such as greater than or equal to 35 wt. %, greater than or equal to 40 wt. %, or even greater than or equal to 45 wt. % multi-ring aromatic compounds having a boiling point temperature greater than or equal to 399° C., based on the unit weight of the pyrolysis oil in the pyrolysis oil feed 102. The pyrolysis oil of the pyrolysis oil feed 102 may also have a low concentration of sulfur and sulfur compounds. The pyrolysis oil feed 102 may have a concentration of sulfur and sulfur-containing compounds of less than or equal to 500 parts per million by weight (ppmw), such as less than or equal to 400 ppmw, or even less than or equal to 300 ppmw.

As previously discussed, in embodiments, the pyrolysis oil feed 102 may include a diluent. Due to the high viscosity of the pyrolysis oil feed 102, the diluent may be added to increase the fluidity of the pyrolysis oil feed 102. The inclusion of the diluent in the pyrolysis oil feed 102 may allow the pyrolysis oil feed 102 to have increased contact with the surfaces of the mixed metal oxide catalyst 106 in the first slurry reactor 110. The diluent may include but is not limited to benzene, mixed xylenes, toluene, or combinations of these. In embodiments, the diluent may be toluene due to the greater solubility of pyrolysis oils in toluene compared to benzene and xylenes. The pyrolysis oil feed 102 may include from 10 wt. % to 90 wt. % diluent based on the total weight of the pyrolysis oil feed 102. The pyrolysis oil feed 102 may include from 10 wt. % to 80 wt. %, from 10 wt. % to 70 wt. %, from 10 wt. % to 60 wt. %, from 30 wt. % to 90 wt. %, from 30 wt. % to 80 wt. %, from 30 wt. % to 70 wt. %, from 30 wt. % to 60 wt. %, from 50 wt. % to 90 wt. %, from 50 wt. % to 80 wt. %, from 50 wt. % to 70 wt. %, from 60 wt. % to 90 wt. %, from 60 wt. % to 80 wt. %, or from 70 wt. % to 90 wt. % diluent based on the total weight of the pyrolysis oil feed 102. In embodiments, pyrolysis oil may be mixed with the diluent in a mixing unit upstream of the first slurry reactor 110 to produce the pyrolysis oil feed 102, which may then be passed to the first slurry reactor 110. In embodiments, the pyrolysis oil feed 102 may not include a diluent added to the pyrolysis oil immediately upstream of the first slurry reactor 110. However, in these embodiments, the pyrolysis oil feed 102 may still include small amounts, such as less than 10 wt. %, toluene, xylene, or benzene that may be carried through or produced from the process producing the pyrolysis oil.

Referring again to FIG. 1, the pyrolysis oil feed 102 may be passed to the slurry reactor 110. The slurry reactor 110 may be operable to contact the pyrolysis oil feed 102 with hydrogen 104 in the presence of the mixed metal oxide catalyst 106 to produce the slurry reactor effluent 114. Contacting the pyrolysis oil feed 102 with hydrogen 104 in the presence of the mixed metal oxide catalyst 106 may convert at least a portion of the multi-ring aromatic compounds in the pyrolysis oil feed 102 to light aromatic compounds. The hydrogen 104 may include a recycled hydrogen stream or supplemental hydrogen from an external hydrogen source inside or outside the battery limits of the refinery. The hydrogen 104 may be passed directly to the slurry reactor 110 or may be combined with the pyrolysis oil feed 102 upstream of the slurry reactor 110. The hydrogen 104 may be used to pressurize the slurry reactor 110 to the operating pressure.

The slurry reactor 110 may include any type of reactor suitable for contacting the pyrolysis oil feed 102 with hydrogen 104 in the presence of the mixed metal oxide catalyst 106. In embodiments, the slurry reactor 110 may comprise a slurry phase reactor. The term "slurry phase reactor" refers to a 3-phase reactor in which a solid phase, liquid phase, and gaseous phase are reacted simultaneously. The slurry phase reactor may include the mixed metal oxide catalyst suspended in the liquid of the pyrolysis oil feed 102 to form the reaction slurry, and the hydrogen may be permeated or bubbled up through the reaction slurry. The slurry phase reactor may be a batch slurry phase reactor or a continuous slurry phase reactor. When the slurry reactor 110 comprises a batch slurry phase reactor, the pyrolysis oil feed 102 and the mixed metal oxide catalyst may be charged to the slurry phase reactor, the slurry reactor sealed, and the hydrogen gas percolated or bubbled through the reaction slurry in the slurry phase reactor. In embodiments, the slurry reactor 110 may comprise one or a plurality of batch slurry phase reactors. When the slurry reactor 110 comprises a plurality of slurry phase reactors, the plurality of slurry phase reactors may be operated in series, in parallel, or a combination thereof. In embodiments, the slurry reactor 110 may include a plurality of batch slurry phase reactors in parallel and the plurality of batch slurry phase reactors may be operated in a staggered manner to approximate continuous operation of the slurry reactor 110.

The mixed metal oxide catalyst 106 may be catalytically active to convert multi-ring aromatic compounds having greater than or equal to tetra-aromatic compounds in the pyrolysis oil feed 102 to light aromatic compounds. The mixed metal oxide catalyst 106 may include a plurality of catalyst particles. Each of the plurality of catalyst particles may include a plurality of different metal oxides. The plurality of metal oxides of the mixed metal oxide catalyst 106 may include oxides of metals in groups 3-13 of the International Union of Pure and Applied Chemistry (IUPAC) periodic table. In embodiments, the plurality of metal oxides of the mixed metal oxide catalyst 106 may include combinations of oxides of iron, zirconium, cerium, aluminum, tungsten, molybdenum, and titanium. The mixed metal oxide catalyst 106 may also include oxides of metalloids, such as oxides of silicon. The mixed metal oxide catalyst 106 may comprise oxides of metals or metalloids selected from the group consisting of iron oxide ($Fe_2O_3$), zirconium oxide ($ZrO_2$), cerium oxide ($CeO_2$), aluminum oxide (alumina) ($Al_2O_3$), silica ($SiO_2$), tungsten oxide ($WO_3$), molybdenum oxide ($MoO_3$), titanium oxide ($TiO_2$), and combinations of these.

The mixed metal oxide catalyst 106 may include iron oxide as one of the plurality of metal oxides. In embodiments, the mixed metal oxide catalyst 106 may include from 60 wt. % to 95 wt. % iron oxide, such as from 70 wt. % to 90 wt. %, from 75 wt. % to 85 wt. %, or from 80 wt. % to 85 wt. % iron oxide. The mixed metal oxide catalyst 106 may include zirconium oxide as one of the plurality of metal oxides. In embodiments, the mixed metal oxide catalyst 106 may include from 1 wt. % to 20 wt. % zirconium oxide, such as from 1 wt. % to 15 wt. %, from 2.5 wt. % to 12.5 wt. %, or from 5 wt. % to 10 wt. % zirconium oxide. The mixed metal oxide catalyst 106 may include cerium oxide as one of the plurality of metal oxides. In embodiments, the mixed metal oxide catalyst 106 may include from 0.1 wt. % to 10 wt. % cerium oxide, such as from 0.5 wt. % to 7.5 wt. %, from 0.5 wt. % to 5 wt. %, or from 1 wt. % to 5 wt. %. The mixed metal oxide catalyst 106 may include aluminum oxide (alumina) as one of the plurality of metal oxides. In embodiments, the mixed metal oxide catalyst 106 may include from 1 wt. % to 20 wt. % aluminum oxide (alumina), such as from 2.5 wt. % to 15 wt. %, from 3 wt. % to 12.5 wt. %, or from 5 wt. % to 10 wt. %. The weight percentages of the plurality of metal oxides of the mixed metal oxide catalyst 106 are based on the total weight of the mixed metal oxide catalyst 106. The mixed metal oxide catalyst 106 may comprise, consist of, or consist essentially of from 60 wt. % to 95 wt. % iron oxide, from 1 wt. % to 20 wt. % zirconium oxide, from 0.1 wt. % to 10 wt. % cerium oxide, and from 1 wt. % to 20 wt. % aluminum oxide (alumina). In embodiments, the mixed metal oxide catalyst 106 may include 83 wt. % iron oxide, 7.5 wt. % zirconium oxide, 2.5 wt. % cerium oxide, and 7.0 wt. % aluminum oxide (alumina). In embodiments, the mixed metal oxide catalyst 106 does not include silica. In embodiments, the mixed metal oxide catalyst 106 may include the plurality of metal oxides mixed and fused or agglomerated together to form the catalyst particles comprising a homogeneous solid mixture of the metal oxides instead of one or more metal oxides deposited on a surface of a support material. The mixed metal oxide catalyst may be prepared by a co-precipitation method to produce the catalyst particles comprising each of the plurality of different metal oxides distributed throughout the catalyst particle.

Contacting the pyrolysis oil feed 102 with hydrogen 104 in the presence of the mixed metal oxide catalyst 106 at the reaction conditions in the slurry reactor 110 may convert at least a portion of the multi-ring aromatic compounds in the pyrolysis oil feed 102 to the light aromatic compounds in a single step, without conducting a subsequent chemical reaction step. Converting at least a portion of the multi-ring aromatic compounds to light aromatic compounds comprising mono-aromatic compounds, di-aromatic compounds, or both, is a complicated reaction scheme comprising multiple synchronized and selective reactions, which may include selective hydrogenation of one aromatic ring in a compound but not all, subsequent ring opening of the saturated tetra-aromatic compounds, hydro-dealkylation, transalkylation, and disproportionation reactions. Not intending to be bound by any particular theory, it is believed that upgrading the pyrolysis oil feed 102 may include selective hydrogenation of at least one aromatic ring structure in a multi-ring aromatic compound to produce a molecule with one or more aromatic rings and at least one saturated ring. The saturated ring portion may then undergo ring opening to produce a substituted aromatic compound. The substituted aromatic may then undergo one or more of hydroalkylation, transalkylation, or disproportionation to produce light aromatic compounds. It is understood that multiple variations and combinations of these reactions as well as other chemical reactions may occur during the upgrading process. This complex sequence of synchronized reactions for upgrading pyrolysis oil feed 102 may be catalyzed using the mixed metal oxide catalyst 106.

The slurry reactor 110 may contact the pyrolysis oil feed 102 with hydrogen 104 in the presence of the mixed metal oxide catalyst 106 at mild operating conditions sufficient to cause at least a portion of multi-ring aromatic compounds in the pyrolysis oil feed 102 to be upgraded to produce a slurry reactor effluent 114, where the slurry reactor effluent 114 comprises light aromatic compounds. The slurry reactor 110 may be operated at an operating temperature in the range of from 350 degrees Celsius (° C.) to 500° C., such as from 400° C. to 500° C., from 350° C. to 450° C., from 400° C. to 450° C., from 380° C. to 420° C., or from 400° C. to 420° C. The hydrocracking reactor 130 may be operated at an operating pressure of from 1 megapascal (MPa) (10 bar) to 5 MPa (50 bar), such as from 2 MPa (20 bar) to 5 MPa (50 bar), from 2.5 MPa (25 bar) to 5 MPa (50 bar), from 3 MPa (30 bar) to 5 MPa (50 bar), from 1 MPa (10 bar) to 4 MPa (40 bar), from 2 MPa (20 bar) to 4 MPa (40 bar), from 2.5 MPa (25 bar) to 4 MPa (40 bar), from 3 MPa (30 bar) to 4 MPa (40 bar), from 1 MPa (10 bar) to 3.5 MPa (35 bar), from 2 MPa (20 bar) to 3.5 MPa (35 bar), from 2.5 MPa (25 bar) to 3.5 MPa (35 bar), from 1 MPa (10 bar) to 3 MPa (30 bar), or from 2 MPa (20 bar) to 3 MPa (30 bar). The slurry reactor 110 may be operated at a volume ratio of hydrogen 104 to the pyrolysis oil in the pyrolysis feed 102 of from 500 to 3000, from 500 to 2500, from 500 to 2000, from 1000 to 3000, from 1000 to 2500, from 1000 to 2000, or from 2000 to 2800. The slurry reactor 110 may be operated at a weight hourly space velocity (WHSV) of from 0.5 per hour ($h^{-1}$) to 2.0 $h^{-1}$, from 0.5 $h^{-1}$ to $h^{-1}$, from 0.5 $h^{-1}$ to 1.0 $h^{-1}$, from 1.0 $h^{-1}$ to 2.0 $h^{-1}$, or from 1.0 $h^{-1}$ to 1.5 $h^{-1}$.

The slurry reactor 110 may include one or more vapor outlets 105 operable to pass gaseous constituents out of the slurry reactor 110 as a gaseous constituent effluent 107. The one or more vapor outlets 105 may be operable to separate the gaseous constituent effluent 107 from the slurry reactor effluent 114 after contacting the pyrolysis oil feed 102 with hydrogen 104 in the presence of the mixed metal oxide 106. The gaseous constituents of the gaseous constituent effluent 107 may include, but are not limited to, excess hydrogen 104, light hydrocarbons (e.g., methane, ethane, etc.), sulfur components (e.g., hydrogen sulfide ($H_2S$)), or combinations of these. The gaseous constituent effluent 107 may include at least 90%, at least 95%, at least 98%, at least 99%, or even at least 99.9% by weight of the gaseous constituents produced in the slurry reactor 110 after upgrading the pyrolysis oil feed 102, where the gaseous constituents generally refer to compounds that are gases at the reaction conditions in the slurry reactor 110. The gaseous constituent effluent 107 may also include excess hydrogen 104. The gaseous constituent effluent 107 may be passed to one or more downstream treatment processes, such as but not limited to processes for recovering any light hydrocarbon compounds from the gaseous constituent effluent 107, separation of excess hydrogen, removal of one or more contaminants, or other processes.

The slurry reactor 110 may be in fluid communication with the slurry reactor effluent separator 120 to pass the slurry reactor effluent 114 from the slurry reactor 110 directly to the slurry reactor effluent separator 120. The slurry reactor effluent 114 may comprise light aromatic compounds. The light aromatic compounds may include mono-aromatic compounds, di-aromatic compounds, or both. The slurry reactor effluent 114 may include at least 90%, at least 95%, at least 98%, at least 99%, or even at least 99.9% by weight of the light aromatic compounds produced in the slurry reactor 110. The slurry reactor effluent 114 may also include the mixed metal oxide catalyst 106 and any unreacted constituents of the pyrolysis oil feed 102, such as unreacted heavy aromatic compounds.

Referring again to FIG. 1, the slurry reactor effluent 114 may be passed to the slurry reactor effluent separator 120. The slurry reactor effluent separator 120 may be directly downstream of the slurry reactor 110 so that the slurry reactor effluent 114 can be passed directly from the slurry reactor 110 to the slurry reactor effluent separator 120 without passing through any intervening reactors or unit operations. The slurry reactor effluent separator 120 may include one or a plurality of separators. The slurry reactor effluent separator 120 may be operable to separate the slurry reactor effluent 114 into at least the intermediate stream 122 and a used mixed metal oxide catalyst 124. The slurry reactor effluent separator 120 may include a solid-liquid separation device operable to separate the slurry reactor effluent 114 into at least one intermediate stream 122 and the used mixed metal oxide catalyst 124. In embodiments, the slurry reactor effluent separator 120 may include a vacuum distillation column. In embodiments, the slurry reactor effluent separator 120 may include a centrifuge. The slurry reactor effluent separator 120 may be operable to separate the slurry reactor effluent 114 by centrifugation into at least the intermediate stream 122 and the used mixed metal oxide catalyst 124. Other solid/liquid separation devices, such as but not limited to filters, settling tanks, cyclonic or separation devices, are contemplated.

Referring again to FIG. 1, in embodiments, the slurry reactor effluent separator 120 may include a vacuum distillation unit 121 and a solid liquid separator 126 downstream of the vacuum distillation unit 121. The vacuum distillation unit 121 may be downstream of the slurry reactor 110 to receive the slurry reactor effluent 114 directly from the slurry reactor 110. The vacuum distillation unit 121 may be operable to separate the slurry reactor effluent 114 into the intermediate stream 122 and a heavy stream 123. The intermediate stream 122 may include the light aromatic compounds, such as the mono-aromatic, di-aromatic compounds, the diluent (if present) and any other light aromatic compounds. The vacuum distillation unit 121 may further be operable to produce one or more product streams (not shown), such as a xylene product stream comprising any xylenes produced in the slurry reactor 110.

The heavy stream 123 may include the used mixed metal oxide catalyst and greater boiling constituents. In embodiments, the greater boiling constituents of the heavy stream 123 may include polyaromatic compounds having greater than 3, greater than 4, or even greater than 5 aromatic rings. The heavy stream 123 may be passed from the vacuum distillation unit 121 to the solid-liquid separator 126, which may be disposed directly downstream from the vacuum distillation unit 121. The heavy stream 123 may be passed directly from the vacuum distillation unit 121 to the solid-liquid separator 126. The solid-liquid separator 126 may be operable to separate the heavy stream 123 to produce the used mixed metal oxide catalyst 124 and a bottom stream 125. The used mixed metal oxide catalyst 124 may include at least 90%, at least 95%, at least 98%, or even at least 99% of the used mixed metal oxide catalyst particles from the heavy stream 123.

The used mixed metal oxide catalyst 124 may be recycled back to the slurry reactor 110. The used mixed metal oxide catalyst 124 may be recycled back to the slurry reactor 110 through a used mixed metal oxide catalyst recycle line. The used mixed metal oxide catalyst recycle line may be fluidly coupled to an outlet of the solid-liquid separator 126 and to an inlet of the slurry reactor 110. The used mixed metal oxide catalyst 124 may be passed from the slurry reactor effluent separator 120, such as a solid-liquid separator 126 of the slurry reactor effluent separator 120, back to the slurry reactor 110.

The bottom stream 125 may be recycled back to the slurry reactor 110. The bottom stream 125 may be recycled back to the slurry reactor 110 through a bottoms recycle line. The bottoms recycle line may be fluidly coupled to an outlet of the slurry reactor effluent separator 120, such as an outlet of the solid-liquid separator 126, and to an inlet of the slurry reactor 110. The bottom stream 125 may be passed from the slurry reactor effluent separator 120, such as the solid-liquid separator 126, back to the slurry reactor 110 for further conversion of polyaromatic compounds from the bottom stream 125 to additional mono-aromatic and di-aromatic compounds. In embodiments, the bottom stream 125 may be mixed with the pyrolysis oil feed 102 upstream of the slurry reactor 110.

Figure 4:
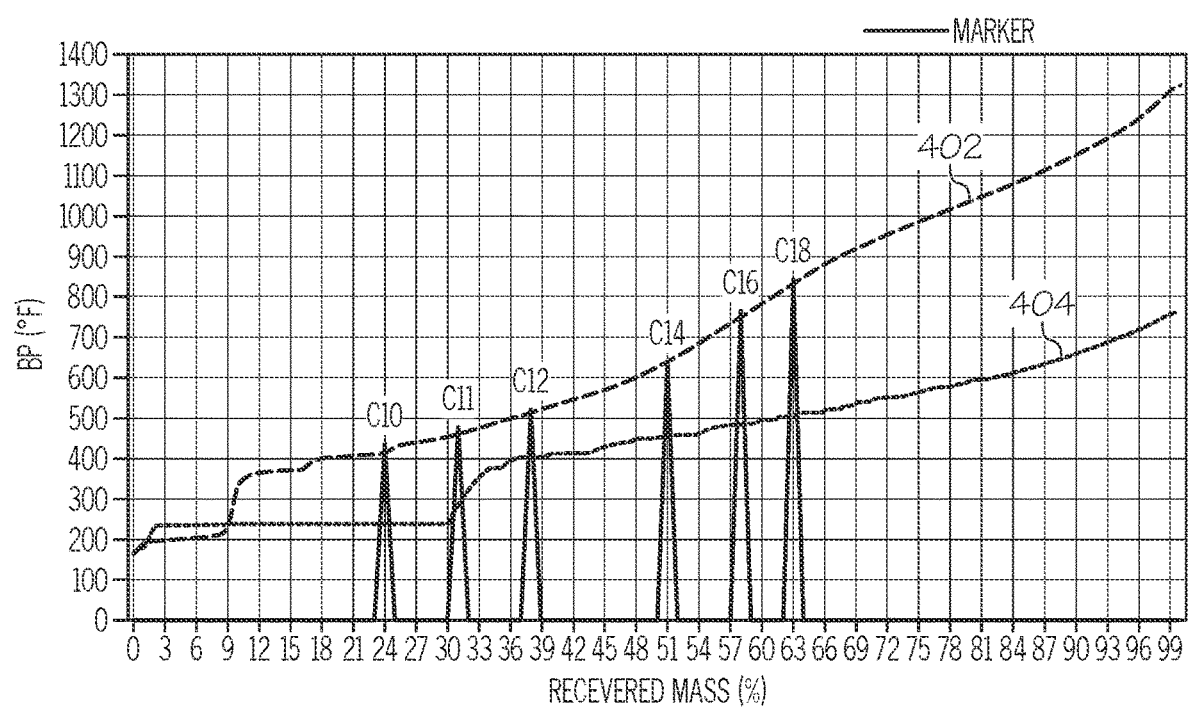
FIG. 4 graphically depicts a boiling point distribution of intermediate stream produced from Example 4, according to one or more embodiments shown and described in this disclosure.

As previously described, the intermediate stream 122 may be passed out of the slurry reactor effluent separator 120 to the hydrocracking reactor 130. The intermediate stream 122 may include di-aromatic compounds, mono-aromatic compounds, or both. The intermediate stream 122 may mainly include mono-aromatic compounds, di-aromatic compounds, or both. The intermediate stream 122 may include at least 90%, at least 95%, at least 98%, at least 99%, or even at least 99.9% by weight of mono-aromatic compounds, di-aromatic compounds, or both from the slurry reactor effluent 114. Referring now to FIG. 4, boiling point distributions for the pyrolysis oil of the pyrolysis oil feed 102 and the intermediate stream 122 from the slurry reactor 110 are graphically depicted. The boiling point distribution for the pyrolysis oil is indicated by reference number 402 in FIG. 4, and the boiling point distribution for the intermediate stream is indicated by reference number 404. Markers indicating the boiling point temperatures for $C_{10}$-$C_{18}$ aromatic compounds is also shown in FIG. 4 for reference. As shown in FIG. 4, the boiling point range for $C_{10}$ to $C_{18}$ aromatic compounds is from around 400 degrees Fahrenheit (° F.) to around 850° F. As shown in FIG. 4, the intermediate stream 122 may include a greater percentage of di-aromatic compounds comprising 10 to 18 carbon atoms compared to the pyrolysis oil of the pyrolysis oil feed 102. The intermediate stream 122 may include at least 35%, at least 40%, at least 45%, at least 50%, or even at least 55% by weight di-aromatic compounds having from 10 to 18 carbon atoms ($C_{10}$ to $C_{18}$ aromatic compounds) based on the total weight of the intermediate stream 122, including any diluent added to the pyrolysis oil feed 102 and passed through the slurry reactor 110. The linear part in the intermediate stream curve 404 shown in FIG. 4 may include toluene added to the pyrolysis oil as the diluent to produce the pyrolysis oil feed 102, but may also include any toluene, benzene, xylene, or ethylbenzene produced in the slurry reactor 110. Mono-aromatic compounds, di-aromatic compounds, or both, included the intermediate stream 122 may be passed to the hydrocracking reactor 130 and then hydrocracked to produce BTEX. The hydrocracking reactor 130 may increase the yields of BTEX and reduce recycle of unreacted pyrolysis oil feed 102 back through the process.

The intermediate stream 122 may be passed downstream to the hydrocracking reactor 130. In embodiments, the intermediate stream 122 may be passed directly from the slurry reactor effluent separator 120 to the hydrocracking reactor 130. In embodiments, the intermediate stream 122 may be passed directly from the vacuum distillation unit 121 if the slurry reactor effluent separator 120 directly to the hydrocracking reactor 130. The hydrocracking reactor 130 may be operable to contact the intermediate stream 122 with hydrogen 132 in the presence of the hydrocracking catalyst 136 to produce a hydrocracking effluent 134. In embodiments, the intermediate stream 122 may be mixed with the hydrogen 132 upstream of the hydrocracking reactor 130 to produce the mixture 133. The mixture 133 may be introduced into the hydrocracking reactor 130. Contacting the intermediate stream 122 with hydrogen 132 in the presence of the hydrocracking catalyst 136 may cause at least a portion of the light aromatic compounds in the intermediate stream 122 to undergo hydrocracking to produce the hydrocracking effluent 134 including aromatic compounds having six to nine carbon atoms. The hydrogen 132 may include a recycled hydrogen stream or supplemental hydrogen from an external hydrogen source inside or outside the battery limits of the refinery. The hydrogen 132 may be passed directly to the hydrocracking reactor 130 or may be combined with the intermediate stream 122 upstream of the hydrocracking reactor 130.

The hydrocracking reactor 130 may include any type of reactor suitable for contacting the intermediate stream 122 with hydrogen 132 in the presence of the hydrocracking catalyst 136. Suitable reactors may include, but are not limited to, batch reactors, fixed bed reactors, moving bed reactors, continuous stirred tank reactors, plug flow reactors, thick liquid attitude bed reactors, boiling-bed reactors, or combinations of reactors. In embodiments, the hydrocracking reactor 130 may comprise a fixed bed reactor. In embodiments, the hydrocracking reactor 130 may comprise one or a plurality of fixed bed reactors operated in series or in parallel.

The hydrocracking catalyst 136 may be operable to cause at least a portion of the light aromatic compounds in the intermediate stream 122 to react to undergo hydrocracking to produce the hydrocracking effluent 134 including aromatic compounds having six to nine carbon atoms. The hydrocracking catalyst 136 may be disposed in a fixed catalyst bed within the hydrocracking reactor 130. The fixed catalyst bed in the hydrocracking reactor 130 may be a hydrocracking reaction zone. The hydrocracking catalyst 136 may include a first metal catalyst and a second metal catalyst supported on a mesoporous zeolite support.

The mesoporous zeolite support may have an average pore size sufficient to enable multi-ring aromatic compounds to access reactive sites within the pores of the mesoporous zeolite support. The mesoporous zeolite support may have an average pore size of greater than or equal to 2 nanometers (nm), greater than or equal to 5 nm, or even greater than or equal to 8 nm as determined using the Barrett-Joyner-Halenda (BJH) method. The mesoporous zeolite support may have an average pore size less than or equal to 40 nm, less than or equal to 30 nm, or even less than or equal to 25 nm as determined using the BJH method. In embodiments, the mesoporous zeolite support may have an average pore size of from 2 nm to 40 nm, from 2 nm to 30 nm, from 2 nm to 25 nm, from 5 nm to 40 nm, from 5 nm to 30 nm, from 5 nm to 25 nm, from 8 nm to 40 nm, from 8 nm to 30 nm, or from 8 nm to 25 nm, where the average pore size is determined using the BJH method. In embodiments, the mesoporous zeolite support may be the hierarchical mesoporous zeolite support.

The mesoporous zeolite support may have a molar ratio of silica ($SiO_2$) to alumina ($Al_2O_3$) of greater than or equal to 10, such as greater than or equal to 20, greater than or equal to 30, greater than or equal to 40, greater than or equal to 50, or greater than or equal to 60. The zeolite support may have a molar ratio of $SiO_2$ to $Al_2O_3$ of less than or equal to 70, such as less than or equal to 60, less than or equal to 50, less than or equal to 40, less than or equal to 30, or even less than or equal to 20. The zeolite support may have a molar ratio of $SiO_2$ to $Al_2O_3$ of from 10 to 70. In embodiments, the zeolite support may have a molar ratio of $SiO_2$ to $Al_2O_3$ of from 10 to 60, from 10 to 50, from 10 to 40, from 20 to 70, from 20 to 60, from 20 to 50, from 20 to 40, from 30 to 70, from 30 to 60, from 30 to 50, from 40 to 70, from 40 to 60, from 50 to 70, or from 10 to 30. In embodiments, the mesoporous zeolite support may be a hierarchical mesoporous beta zeolite support. In embodiments, the hierarchical mesoporous beta zeolite support may have an average pore size of 2 nm to 40 nm, or from 5 nm to 25 nm.

In embodiments, the mesoporous zeolite support may be a hierarchical mesoporous zeolite support prepared from a parent microporous zeolite through a desilication process, in which silica may be removed from the zeolite to create a mesoporous structure and increase the average pore size. A desilication method of preparing the hierarchical mesoporous zeolite support may include providing a microporous parent zeolite with a silica to alumina ($SiO_2/Al_2O_3$) ratio of at least 5 or greater than or equal to 20, mixing the microporous parent zeolite with an aqueous metal hydroxide solution, and heating the microporous parent zeolite and aqueous metal hydroxide mixture to temperatures greater than or equal to 100° C. to produce the mesoporous zeolite supports having an average pore size greater than 2 nm, greater than or equal to 5 nm, or even greater than or equal to 8 nm as determined using the BJH method. In embodiments, the mesoporous zeolite supports may be produced without a templating agent or a pore-directing agent.

As used in the present disclosure, microporous zeolites refer to zeolite particles that have an average pore size of less than 2 nm, such as less than 1 nm as determined using the BJH method. The microporous zeolites may have an average particle size, as measured by their longest dimension, of less than or equal to 10 micrometer (μm), less than or equal to 8 μm, less than or equal to 6 μm, less than or equal to 4 μm, less than or equal to 2 μm, or less than or equal to 1 μm. The microporous zeolites may have an average particle size, as measured by their longest dimension, of greater than or equal to 0.1 μm, greater than or equal to 0.2 μm, or greater than or equal to 0.5 μm. In embodiments, the microporous parent zeolite particles are present as a single crystal structure. The microporous parent zeolites may have an average particle size from 0.1 μm to 10 μm, from 0.1 μm to 8 μm, from 0.1 μm to 6 μm, from 0.1 μm to 4 μm, from 0.1 μm to 2 μm, from 0.1 mm to 1 μm, from 0.2 μm to 10 μm, from 0.2 μm to 8 μm, from 0.2 μm to 6 μm, from 0.2 μm to 4 μm, from 0.2 μm to 2 μm, from 0.2 mm to 1 μm, from 0.5 μm to 10 μm, from 0.5 μm to 8 μm, from 0.5 μm to 6 μm, from 0.5 μm to 4 μm, from 0.5 μm to 2 μm, or from 0.5 mm to 1 μm. The average particle size of a zeolite may refer to the average value of the particle size of all the particles of a zeolite in a given sample. In embodiments, the microporous parent zeolite may have a molar ratio of silica to alumina ($SiO_2/Al_2O_3$) of at least 5, at least 15, at least 20, at least 25, at least 30, or even at least 35. In embodiments, the microporous parent zeolite may have a molar ratio of silica to alumina of from 5 to 100, from 5 to 90, from 5 to 80, from 20 to 100, from 20 to 90, from 20 to 80, from 20 to 70, from 20 to 66, from 25 to 100, from 25 to 90, from 25 to 80, from 25 to 70, from 25 to 66, from 30 to 100, from 30 to 90, from 30 to 80, from 30 to 70, from 30 to 66, from 35 to 100, from 35 to 90, from 35 to 80, from 35 to 70, or even from 35 to 66. In embodiments, the microporous parent zeolite may be a beta zeolite.

Although a desilication method for producing the mesoporous zeolite support is described in the present disclosure, it is understood that any other process known in the art may also be used to produce the mesoporous zeolite support. Methods for producing mesoporous zeolite supports may include, but are not limited to, other "top down" methods conducted at temperatures less than 100° C., which may include utilizing pore-directing agents to facilitate formation of mesoporous. "Top down" methods may refer to methods in which a parent zeolite is chemically eroded to produce the mesoporous structure. Another method for producing mesoporous zeolite supports may include "bottom up" methods, which include building up the mesoporous zeolite from zeolite precursors. In the "bottom up" methods, templating agents are included and the zeolite is built-up around the templating agents to form the mesoporous structure. The resulting zeolite is then calcined to burn off the templating agent to produce the mesoporous zeolite support. Other synthesis methods may also be used to produce the mesoporous zeolite.

The hydrocracking catalyst 136 may be prepared from the mesoporous zeolite support by wet impregnation of at least a first metal catalyst precursor and a second metal catalyst precursor onto the outer surfaces, pore surfaces, or both, of the mesoporous zeolite support.

As previously described, the hydrocracking catalyst 136 may include the first metal catalyst and the second metal catalyst supported on the mesoporous zeolite support. At least one of the first metal catalyst and the second metal catalyst may include a heteropolyacid. The heteropolyacid may include at least one metal selected from cobalt, molybdenum, vanadium, or combinations thereof, and at least one heteroatom selected from phosphorous (P), silicon (Si), arsenic (As), germanium (Ge), or combinations of these. The heteropolyacid may also include oxygen. Heteropolyacids suitable for the first metal catalyst, the second metal catalyst, or both may have a Keggin structure having general formula $XM_{12}O_{40}{}^{n-}$ or a Dawson structure having the general formula $XM_{18}O_{82}{}^{n-}$, in which X is the heteroatom selected from phosphorous, silicon, arsenic, germanium, or combinations of these; M is the molybdenum and optionally one or more of cobalt, vanadium, or a combination of these; and n– is an integer indicative of the charge of the anion of the heteropolyacid. Examples of heteropolyacids may include, but are not limited to phosphormolybdic heteropolyacid ($H_3PMo_{12}O_{40}$), decamolybdiccobaltate heteropolyacid ($H_6[Co_2Mo_{10}O_{38}H_4]$), silicomolybdic heteropolyacid ($H_4SiMo_{12}O_{40}$), $H_4[PCoMo_{11}O_{40}]$, $H_4[PVMo_{11}O_{40}]$, $H_5[PV_2Mo_{10}O_{40}]$, $H_7[PV_4Mo_8O_{40}]$, $H_9[PV_6Mo_6O_{40}]$, $H_3[AsMo_{12}O_{40}]$, $H_4[AsCoMo_{11}O_{40}]$, $H_5[AsCo_2Mo_{10}O_{40}]$, $H_4[AsVMo_{11}O_{40}]$, $H_5[AsV_2Mo_{10}O_{40}]$, $H_7[AsV_4Mo_8O_{40}]$, $H_9[AsV_6Mo_6O_{40}]$, $H_5[SiCoMo_{10}O_{40}]$, $H_6[SiCo_2Mo_{10}O_{40}]$, $H_5[SiVMo_{10}O_{40}]$, $H_6[SiV_2Mo_{10}O_{40}]$, $H_{10}[SiV_6Mo_6O_{40}]$, $H_6[P_2Mo_{18}O_{82}]$, other heteropolyacids, salts of these heteropolyacids, or combinations of heteropolyacids. Salts of these heteropolyacids may include alkali metal salts, alkaline earth metal salts, nitrate salts, sulfate salts, or other salts of the heteropolyacid. Alkali metals may include sodium, potassium, rubidium, cesium, or combinations of these. Alkaline earth metals may include, but are not limited to magnesium, calcium, or combinations of these. In embodiments, the heteropolyacid may include phosphormolybdic heteropolyacid having formula $H_3[PMo_{12}O_{40}]$. In embodiments, the heteropolyacid may include decamolybdodicobaltate heteropolyacid having chemical formula $H_6[Co_2Mo_{10}O_{38}H_4]$. In embodiments, the heteropolyacid may be silicomolybdic heterpolyacid having chemical formula $H_4[SiMo_{12}O_{40}]$. In embodiments, the first metal catalyst, the second catalyst, or both may be a metal salt of a heteropolyacid, such as an alkali metal salt or alkaline metal salt of the heteropolyacid.

Still referring to FIG. 1, the first metal catalyst, the second metal catalyst, or both may be a heteropolyacid. In embodiments, the first metal catalyst may include a heteropolyacid, and the second metal catalyst may include a non-heteropolyacid. In embodiments, both the first metal catalyst and the second metal catalyst may include heteropolyacids. In embodiments, the first metal catalyst may include a first heteropolyacid, and the second metal catalyst may include a second heteropolyacid that is different from the first heteropolyacid. For example, in embodiments, the first metal catalyst may include a first heteropolyacid that includes molybdenum as the metal, and the second metal catalyst may include a second heteropolyacid that includes cobalt as the metal. In embodiments, the first metal catalyst and the second metal catalyst may include the same heteropolyacid, and the heteropolyacid may include a first metal, a second metal that is different from the first metal, and at least one heteroatom. In embodiments, the first metal and the second metal may be cobalt and molybdenum, respectively. In embodiments, the hydrocracking catalyst 136 may include from 0 wt. % to 25 wt. % molybdenum and from 0 wt. % to 10 wt. % of cobalt, such as from 0.01 wt. % to 25 wt. % molybdenum and from 0.01 wt. % to 10 wt. % cobalt, based on the total weight of the hydrocracking catalyst 136. The hydrocracking catalyst 136 may include from 11 wt. % to 13 wt. % molybdenum and from 3 wt. % to 4 wt. % cobalt based on the total weight of the hydrocracking catalyst 136.

The hydrocracking catalyst 136 may further include phosphorous. The phosphorous may be provided by the heteropolyacids used to provide the first metal catalyst, the second metal catalyst, or both. Alternatively or additionally, the phosphorous may be provided by a separate phosphorous-containing compound, such as but not limited to phosphoric acid, phosphorous acid, or other phosphorous-containing compounds, which may be added during synthesis of the hydrocracking catalyst 136.

Contacting the intermediate stream 122 with hydrogen 132 in the presence of the hydrocracking catalyst 136 at the reaction conditions may cause at least a portion of the light aromatic compounds in the intermediate stream 122 to undergo hydrocracking to produce aromatic compounds having six to nine carbon atoms in a single step, without conducting a subsequent chemical reaction step. Converting at least a portion of the light aromatic compounds in the intermediate stream 122 to aromatic compounds having six to nine carbon atoms is also a complicated reaction scheme comprising multiple synchronized and selective reactions, which may include selective hydrogenation of one aromatic ring in a compound but not all, subsequent ring opening of the saturated naphthenic ring, hydro-dealkylation, transalkylation, and disproportionation reactions. Not intending to be bound by any particular theory, it is believed that upgrading intermediate stream 122 may include selective hydrogenation of at least one aromatic ring structure of a multi-ring aromatic compound, such as the mono-aromatic compounds, di-aromatic compounds, or both, in the intermediate stream 122, to produce a molecule with one aromatic ring and at least one saturated ring. The saturated rings may then undergo ring opening to produce substituted aromatic compounds. The substituted aromatic may then undergo one or more of hydroalkylation, transalkylation, or disproportionation to produce the aromatic compounds having six to nine carbon atoms, such as BTEX. It is understood that multiple variations and combinations of these reactions as well as other chemical reactions may occur during the upgrading process in the hydrocracking reactor 130 as well. This complex sequence of synchronized reactions for upgrading the light aromatic compounds in the intermediate stream 122 may be catalyzed using the hydrocracking catalyst 136.

The hydrocracking reactor 130 may contact the intermediate stream 122 with hydrogen 132 in the presence of the hydrocracking catalyst 136 at operating conditions sufficient to cause at least a portion of the light aromatic compounds in the intermediate stream 122 to react to form aromatic compounds having six to nine carbon atoms. The hydrocracking reactor 130 may be operated at an operating temperature in the range of from 350° C. to 500° C., such as from 400° C. to 500° C., from 350° C. to 450° C., from 400° C. to 450° C., from 380° C. to 420° C., or from 400° C. to 420° C. The hydrocracking reactor 130 may be operated at an operating pressure of from 1 MPa (10 bar) to 5 MPa (50 bar), such as from 2 MPa (20 bar) to 5 MPa (50 bar), from 2.5 MPa (25 bar) to 5 MPa (50 bar), from 3 MPa (30 bar) to 5 MPa (50 bar), from 1 MPa (10 bar) to 4 MPa (40 bar), from 2 MPa (20 bar) to 4 MPa (40 bar), from 2.5 MPa (25 bar) to 4 MPa (40 bar), from 3 MPa (30 bar) to 4 MPa (40 bar), from 1 MPa (10 bar) to 3.5 MPa (35 bar), from 2 MPa (20 bar) to 3.5 MPa (35 bar), from 2.5 MPa (25 bar) to 3.5 MPa (35 bar), from 1 MPa (10 bar) to 3 MPa (30 bar), or from 2 MPa (20 bar) to 3 MPa (30 bar). The hydrocracking reactor 130 may be operated at a volume ratio of hydrogen 132 to the light aromatic compounds of from 500 to 3000, from 500 to 2500, from 500 to 2000, from 1000 to 3000, from 1000 to 2500, from 1000 to 2000, or from 2000 to 2800. The hydrocracking reactor 130 may be operated at WHSV of from 0.5 $h^{-1}$ to 2.0 $h^{-1}$, from 0.5 $h^{-1}$ to 1.5 $h^{-1}$, from 0.5 $h^{-1}$ to 1.0 $h^{-1}$, from 1.0 $h^{-1}$ to 2.0 $h^{-1}$, or from 1.0 $h^{-1}$ to 1.5 $h^{-1}$.

The hydrocracking reactor 130 may produce a hydrocracking effluent 134 that may be passed out of the hydrocracking reactor 130. The hydrocracking effluent 134 may include the aromatic compounds having six to nine carbon atoms produced in the hydrocracking reactor 130. The aromatic compounds having six to nine carbon atoms may include benzene, toluene, ethyl-benzene, xylenes, or combinations thereof. Other aromatic compounds having six to nine carbon atoms may also be present in the hydrocracking effluent 134. The hydrocracking effluent 134 may also include light gaseous constituents and unreacted light aromatic compounds from the intermediate stream 122. The light gaseous constituents of the hydrocracking effluent 134 may include, but are not limited to, excess hydrogen 132, light hydrocarbons (e.g., methane, ethane, etc.) produced in the hydrocracking reactor 130, sulfur components (e.g., hydrogen sulfide ($H_2S$)), or combinations of these. The light gaseous constituents of the hydrocracking effluent 134 generally include compounds that are gases at atmospheric conditions.

The hydrocracking reactor 130 may be in fluid communication with the transalkylation reactor 140 to pass the hydrocracking effluent 134 directly from an outlet of the hydrocracking reactor 130 to an inlet of the transalkylation reactor 140. The aromatic compounds having six to nine carbon atoms included in the hydrocracking effluent 134 may be passed to the transalkylation reactor 140. The transalkylation reactor 140 may be operable to contact the hydrocracking effluent 134 with hydrogen in the presence of a transalkylation catalyst 146 at reaction conditions sufficient to cause at least a portion of the aromatic compounds having six to nine carbon atoms to undergo transalkylation to produce xylenes. The transalkylation reactor 140 may increase the yields of xylenes and reduce recycle of unreacted pyrolysis oil feed 102, unreacted hydrocracking effluent 134, or both back through the process.

The transalkylation reactor 140 may include any type of reactor suitable for contacting the hydrocracking effluent 134 with hydrogen 142 in the presence of the transalkylation catalyst 146. Suitable reactors may include, but are not limited to, batch reactors, fixed bed reactors, moving bed reactors, continuous stirred tank reactors, plug flow reactors, thick liquid attitude bed reactors, boiling-bed reactors, or combinations of reactors. In embodiments, the transalkylation reactor 140 may comprise a fixed bed reactor. In embodiments, the transalkylation reactor 140 may comprise one or a plurality of fixed bed reactors operated in series or in parallel.

The transalkylation catalyst 146 may be operable to cause at least a portion of the aromatic compounds in the hydrocracking effluent 134 to react to produce a transalkylation effluent 144 comprising xylenes. The transalkylation catalyst may have a mesostructure comprising at least one disordered mesophase and at least one ordered mesophase. As used in this disclosure, the term "ordered mesophase" may refer to a crystalline zeolite having a uniform arrangement of mesopores, where "mesopores" have an average pore diameter between 2 nm and 50 nm. The term "disordered mesophase" may refer to a non-uniform arrangement of mesopores, where mesopores have an average pore diameter between 2 nm and 50 nm. The term "ordered/disordered phase" may refer to the surface having a combination of at least one ordered mesophase and at least one disordered mesophase. Induction of an ordered/disordered phase into the zeolite structure increases the probability of larger molecules in a feed having access to the active sites inside the transalkylation catalyst 146.

The transalkylation catalyst 146 may include a solid zeolite composite and a metal. The solid zeolite composite may include ZSM-5, ZSM-11, ZSM-12, ZSM-22, ZSM-23, Mordenite (MOR) framework zeolite, NES topology zeolite, EU-1, MAPO-36, SAPO-5, SAPO-11, SAPO-34, SAPO-41, or combinations of these. The solid zeolite composite may include mesoporous Mordenite (MOR) zeolite and mesoporous ZSM-5 zeolite in a 1:1 to 5:1 weight ratio. The mesoporous Mordenite (MOR) zeolite may have a Si/Al molar ratio of at least 20, of from 20 to 300, of from 20 to 100, of from 25 to 50, or of from 28 to 32. In embodiments, the mesoporous ZSM-5 zeolite may have a Si/Al molar ratio of at least 5, such as from 5 to 500, from 10 to 100, from 20 to 75, from 30 to 50, from 35 to 45, or from 38 to 42. The transalkylation catalyst 146 may further include the metal comprising molybdenum, platinum, rhenium, nickel, or combinations thereof. In embodiments, the transalkylation catalyst 146 may include from 1 wt. % to 10 wt. %, from 1 wt. % to 8 wt. %, from 1 wt. % to 6 wt. %, from 1 wt. % to 5 wt. %, from 2 wt. % to 10 wt. %, from 2 wt. % to 8 wt.

%, from 2 wt. % to 6 wt. %, or from 2 wt. % to 5 wt. % metal based on the total weight of the transalkylation catalyst 146.

In embodiments, the transalkylation catalyst 146 may be prepared through a wet impregnation process. A wet impregnation method may include mixing two zeolites selected from the group consisting of ZSM-5, ZSM-11, ZSM-12, ZSM-22, ZSM-23, Mordenite zeolite, NES topology zeolite, EU-1, MAPO-36, SAPO-5, SAPO-11, SAPO-34, and SAPO-41 to form a solid zeolite composite. The solid zeolite composite may then be mixed with a binder including inorganic oxides, such as one or more of alumina, magnesia, zirconia, chromia, titania, boric, phosphate, zinc oxide, and silica, to form extrudates. In embodiments, the ratio by weight of solid zeolite composite to binder is 4 to 1 (80 wt. % solid zeolite composite and 20 wt. % binder), 3 to 1 (75 wt. % solid zeolite composite and 24 wt. % binder), or 2 to 1 (67 wt. % solid zeolite composite and 33 wt. % binder). The extrudates may be loaded with a metal through a wet impregnation process. Although a wet impregnation method for producing the transalkylation catalyst 146 is described in the present disclosure, it is understood that any other process known in the art may also be used to produce the transalkylation catalyst 146.

Contacting the hydrocracking effluent 134 with hydrogen 142 in the presence of the transalkylation catalyst 146 at the reaction conditions may cause at least a portion of the aromatic compounds in the hydrocracking effluent 134 to undergo transalkylation to produce xylenes in a single step, without conducting a subsequent chemical reaction step. Converting at least a portion of the aromatic compounds in the hydrocracking effluent 134 to xylenes is also a reaction scheme comprising transferring of an alkyl group from one aromatic compound to another. The transalkylation reaction can include the transfer of methyl and ethyl groups between benzene rings. Not intending to be bound by any particular theory, it is believed that upgrading hydrocracking effluent 134 may include transalkylation of toluene in the hydrocracking effluent 134 to form benzene and xylene. This transalkylation reaction for upgrading hydrocracking effluent 134 may be catalyzed using the transalkylation catalyst 146.

The transalkylation reactor 140 may contact the hydrocracking effluent 134 with hydrogen 104 in the presence of the transalkylation catalyst 146 at mild operating conditions sufficient to cause at least a portion of aromatic compounds having 6 to 9 carbon atoms in the hydrocracking effluent 134 to be upgraded to produce a transalkylation effluent 144, where the transalkylation effluent 144 comprises xylenes. The transalkylation reactor 140 may be operated at an operating temperature in the range of from 350° C. to 500° C., from 400° C. to 500° C., from 350° C. to 450° C., or from 400° C. to 450° C. The transalkylation reactor 140 may be operated at an operating pressure of from 1 MPa (10 bar) to 5 MPa (50 bar), such as from 1.5 MPa (15 bar) to 5 MPa (50 bar), from 2 MPa (20 bar) to 5 MPa (50 bar), from 3 MPa (30 bar) to 5 MPa (50 bar), from 1 MPa (10 bar) to 4 MPa (40 bar), from 1.5 MPa (15 bar) to 4 MPa (40 bar), from 2 MPa (20 bar) to 4 MPa (40 bar), from 3 MPa (30 bar) to 4 MPa (40 bar), from 1 MPa (10 bar) to 3 MPa (30 bar), from 1.5 MPa (15 bar) to 3 MPa (30 bar), from 2 MPa (20 bar) to 3 MPa (30 bar), from 1 MPa (10 bar) to 2.5 MPa (25 bar), from 1.5 MPa (15 bar) to 2.5 MPa (25 bar), or from 2 MPa (20 bar) to 2.5 MPa (25 bar). The transalkylation reactor 140 may be operated at a volume ratio of hydrogen 142 to the hydrocracking effluent 134 of from 500 to 1500, or from 500 to 1000. The transalkylation reactor 140 may be operated at WHSV of from $0.5\ h^{-1}$ to $5.0\ h^{-1}$, from $0.5\ h^{-1}$ to $4.0\ h^{-1}$, from $0.5\ h^{-1}$ to $3.0\ h^{-1}$, from $1.0\ h^{-1}$ to $5.0\ h^{-1}$, from $1.0\ h^{-1}$ to $4.0\ h^{-1}$, from $1.0\ h^{-1}$ to $3.0\ h^{-1}$, from $2.0\ h^{-1}$ to $5.0\ h^{-1}$, from $2.0\ h^{-1}$ to $4.0\ h^{-1}$, from $2.0\ h^{-1}$ to $3.0\ h^{-1}$, from $3.0\ h^{-1}$ to $5.0\ h^{-1}$, from $3.0\ h^{-1}$ to $4.0\ h^{-1}$, or from $4.0\ h^{-1}$ to $5.0\ h^{-1}$.

The system 100 may include a transalkylation effluent separator 150 disposed downstream of the transalkylation reactor 140. The transalkylation reactor 140 may be in fluid communication with the transalkylation effluent separator 150 to pass the transalkylation effluent 144 from an outlet of the transalkylation reactor 140 directly to an inlet of the transalkylation effluent separator 150. The transalkylation effluent 144 may comprise xylenes.

The transalkylation effluent separator 150 may include one or a plurality of separators. The transalkylation effluent separator 150 may be operable to separate the transalkylation effluent 144 into at least a light gas effluent 151 and a xylene-containing effluent 152. The transalkylation effluent separator 150 may further be operable to produce a transalkylation bottom stream 153. Although the transalkylation effluent separator 150 is depicted in FIG. 1 as separating the transalkylation effluent 144 into the light gas effluent 151, the xylene-containing effluent 152, and the transalkylation bottom stream 153, it is understood that the transalkylation effluent separator 150 may be operable to separate the transalkylation effluent 144 into a plurality of product effluents, at least one of which may be a xylene-containing effluent 152 comprising mixed xylenes. The transalkylation effluent separator 150 may include a distillation unit, vacuum distillation unit, or fractionation unit. In embodiments, the transalkylation effluent separator 150 may include a vacuum distillation column.

The xylene-containing effluent 152 may include mixed xylenes produced in the transalkylation reactor 140. The xylene-containing effluent 152 may include at least 90%, at least 95%, at least 98%, at least 99%, or at least 99.9% of the mixed xylenes from the transalkylation effluent 144. The xylene-containing effluent 152 may be passed to one or more downstream processes for further separation, treatment, or processing. The light gas effluent 151 may include, but are not limited to, excess hydrogen 142, xylenes produced in the transalkylation reactor 140, sulfur components (e.g., hydrogen sulfide ($H_2S$)), or combinations of these. The light gas effluent 151 generally includes compounds that are gases at atmospheric conditions.

The transalkylation bottom stream 153 may be recycled from the transalkylation effluent separator 150 back to the hydrocracking reactor 130, the transalkylation reactor 140, or both. The transalkylation bottom stream 153 may be recycled back to the hydrocracking reactor 130, the transalkylation reactor 140, or both through a transalkylation bottoms recycle line. The transalkylation bottoms recycle line may be fluidly coupled to an outlet of the transalkylation effluent separator 150 and to an inlet of the hydrocracking reactor 130, an inlet of the transalkylation reactor 140, or both. The transalkylation bottom stream 153 may be passed from the transalkylation effluent separator 150 back to the hydrocracking reactor 130, the transalkylation reactor 140, or both for further conversion of polyaromatic compounds from the transalkylation bottom stream 153 to additional xylene. In embodiments, the transalkylation bottom stream 153 may be mixed with the intermediate stream 122 upstream of the hydrocracking reactor 130, the hydrocracking effluent 134 upstream of the transalkylation reactor 140, or both.

Upgrading pyrolysis oil feed 102 by a three stage catalytic process of the present disclosure may produce a greater yield of benzene, toluene, ethylbenzene, xylenes, or combinations of these, compared to upgrading the pyrolysis oil by conventional single stage catalytic process. In embodiments, the systems 100 of the present disclosure may produce a combined yield of benzene, toluene, ethylbenzene, xylenes, or combinations of these, of greater than or equal to 50 wt. %, greater than or equal to 55 wt. %, or even greater than or equal to 60 wt. %, based on the total weight of the pyrolysis oil of the pyrolysis oil feed 102 introduced to the three stage catalytic process of the present disclosure.

Referring again to FIG. 1, a method for upgrading pyrolysis oil feed 102 may include contacting the pyrolysis oil feed 102 with hydrogen 104 in the presence of a mixed metal oxide catalyst 106 at reaction conditions to produce a slurry reactor effluent 114 comprising light aromatic compounds. As previously described in the present disclosure, contacting the pyrolysis oil feed 102 with hydrogen 104 in the presence of the mixed metal oxide catalyst 106 at the reaction conditions may convert at least a portion of the multi-ring aromatic compounds in the pyrolysis oil feed 102 to light aromatic compounds. The reaction conditions may include: (a) a temperature of from 350° C. to 500° C.; (b) a pressure of from 1 MPa (10 bar) to 5 MPa (50 bar); (c) a volume ratio of hydrogen to the pyrolysis oil of from 500 to 3000; (d) WHSV of from 0.5 $h^{-1}$ to 2.0 $h^{-1}$, or combinations of.

The slurry reactor 110 may have any of the features, catalysts, or operating conditions previously discussed in this disclosure for the slurry reactor 110. The method may also include separating the slurry reactor effluent 114 in the slurry reactor effluent separator 120 to produce the intermediate stream 122 and the used mixed metal oxide catalyst 124. The slurry reactor effluent separator 120 may have any of the features, catalysts, or operating conditions previously discussed in this disclosure for the slurry reactor effluent separator 120.

The method may include passing the intermediate stream 122 comprising the light aromatic compounds to a hydrocracking reactor 130 downstream of the slurry reactor 110. The method may include contacting the intermediate stream 122 with hydrogen 132 in the presence of a hydrocracking catalyst 136 at reaction conditions to produce a hydrocracking effluent 134 comprising aromatic compounds having six to nine carbon atoms. As previously described in the present disclosure, contacting the intermediate stream 122 with hydrogen 132 in the presence of the hydrocracking catalyst 136 at the reaction conditions may cause at least a portion of the light aromatic compounds in the intermediate stream 122 to produce the hydrocracking effluent 134 including aromatic compounds having six to nine carbon atoms. The reaction conditions may include: (a) a temperature of from 350° C. to 500° C.; (b) a pressure of from 1 MPa (10 bar) to 5 MPa (50 bar); (c) a volume ratio of hydrogen to the light aromatic compounds of from 500 to 3000; (d) WHSV of from 0.5 $h^{-1}$ to 2.0 $h^{-1}$, or combinations of.

The hydrocracking reactor 130 may have any of the features, catalysts, or operating conditions previously discussed in this disclosure for the hydrocracking reactor 130. The method may also include passing the hydrocracking effluent 134 from the hydrocracking reactor 130 to the transalkylation reactor 140. The method may further include contacting the hydrocracking effluent 134 with hydrogen 142 in the presence of the transalkylation catalyst 146 in the transalkylation reactor 140. As previously described in the present disclosure, contacting the hydrocracking effluent 134 with hydrogen 142 in the presence of the transalkylation catalyst 146 may cause at least a portion of the aromatic compounds in the hydrocracking effluent 134 to undergo transalkylation to produce the transalkylation effluent 144 comprising xylenes. The reaction conditions may include: (a) a temperature of from 350° C. to 500° C.; (b) a pressure of from 1 MPa (10 bar) to 5 MPa (50 bar); (c) a volume ratio of hydrogen 142 to the hydrocracking effluent 134 of from 500 to 1500; (d) WHSV of from 0.5 $h^{-1}$ to 5.0 $h^{-1}$, or combinations of these.

The method may also include separating the hydrocracking effluent 134 in the transalkylation effluent separator 150 to produce the light gas effluent 151, the xylene containing effluent 152 comprising the xylenes, and the transalkylation bottom stream 153. The transalkylation effluent separator 150 may have any of the features, catalysts, or operating conditions previously discussed in this disclosure for the transalkylation effluent separator 150. The methods may include passing the transalkylation bottom stream 153 back to the hydrocracking reactor 130 or back to the transalkylation reactor 140.

EXAMPLES

The various embodiments of methods and systems for the processing of pyrolysis oils will be further clarified by the following examples. The examples are illustrative in nature, and should not be understood to limit the subject matter of the present disclosure.

Example 1: Mixed Metal Oxide Catalyst Preparation

To prepare a mixed metal oxide catalyst comprising iron oxide, zirconium oxide, cerium oxide, and aluminum oxide, 40 grams (g) of iron(III) nitrate nonahydrate ($Fe(NO_3)_3.9H_2O$) was dissolved in 800 milliliters (mL) of distilled water to make Solution A. Then, the other metal oxide precursors were added into Solution A. Specifically, 4.906 g of aluminum nitrate nonahydrate ($Al(NO_3)_3.9H_2O$), 1.549 g of zirconium(IV) oxynitrate hydrate ($ZrO(NO_3)_2:3H_2O$), and 0.601 g of cerium(III) nitrate hexahydrate ($Ce(NO_3)_3.6H_2O$) were added into Solution A to form Solution B. Solution B was then stirred for thirty minutes.

An ammonia solution, Solution C, was prepared by adding 40 mL ammonium hydroxide ($NH_4OH$) (28-30 percentages (%) $NH_3$ basis) in 60 mL distilled water. Solution C was added slowly into Solution B to produce Solution D. Solution C was added until the pH value of Solution D reached roughly 7. Solution D was then stirred for another hour.

After preparing Solution D and another hour of stirring, the precipitate was separated from Solution D and dried in an oven overnight (i.e., for about twelve hours). The dried precipitate was then calcined in air at 500 degrees Celsius (° C.) for two hours. After calcining, the dried and calcined precipitate was crushed to obtain the final mixed metal oxide catalyst comprising iron oxide, alumina, cerium oxide, and zirconium oxide.

Example 2: Hydrocracking Catalyst Preparation

In Example 2, the hydrocracking catalyst was prepared by first upgrading the zeolite support to a hierarchical mesoporous zeolite support. The first metal catalyst, second metal catalyst, and phosphorous were then deposited on the outer surfaces and pore surface of the hierarchical mesoporous zeolite support using a heteropolyacid for the first metal catalyst precursor and phosphorous.

The starting beta zeolite was HSZ-931 HOA beta zeolite obtained from Tosoh, which is a micrometer-sized beta zeolite having a molar ratio of silica to alumina ($SiO_2$/

Al₂O₃) of 28. The beta zeolite was converted to hierarchical mesoporous beta zeolite by adding 22.2 grams of the HSZ-931 HOA beta zeolite to 600 mL of a 0.2 molar (M) solution of NaOH. The mixture was then subjected to hydrothermal desilication at a temperature of 150° C. for 21 hours. The hierarchical mesoporous beta zeolite had a final molar ratio of silica to alumina after the conversion of 20. The hierarchical mesoporous beta zeolite had an average pore size of 10 nm with a peak pore size in the range of 20-25 nm, as determined by the methods previously discussed in this disclosure. The hierarchical mesoporous beta zeolite also had a pore volume of 0.59 cubic centimeters per gram.

The hierarchical mesoporous beta zeolite were ion-exchanged in 0.8 M solution of ammonium nitrate ($NH_4NO_3$) at 80° C. for 2 hours for three times (the ratio of 1 g zeolite to 10 ml $NH_4NO_3$ solution). The ion-exchanged zeolites were dried at 110° C. and then calcined at 550° C. for five hours with a heating rate of 5 degrees Celsius per minute (° C./min).

The acidity of the hierarchical mesoporous beta zeolite was adjusted by dealumination in a diluted nitric acid solution. In particular, for Example 2, the hierarchical mesoporous beta zeolite was dealimunated by contacting the hierarchical mesoporous beta zeolite with a 0.2 M solution of nitric acid ($HNO_3$) at 80° C. for a period of 2 hours. The dealuminated hierarchical mesoporous beta zeolite was then ion-exchanged in a 0.8 M solution of ammonium nitrate ($NH_4NO_3$) for 2 hours at 80° C. one time. The ion-exchanged dealuminated hierarchical mesoporous beta zeolite was then dried and calcined at 550° C. for 5 hours to produce the hierarchical mesoporous beta zeolite support of Example 2, which is referred to in this disclosure as Beta-M50 zeolite support.

The hydrocracking catalyst of Example 2 was then produced by adding 5 grams of the Beta-M50 zeolite support to a round bottom flask. Solution A was prepared by dissolving 1.44 grams of the heteropolyacid of the first metal catalyst precursor [$H_3PMo_{12}O_{40}$] in 15 mL of distilled water. Solution B was then prepared by dissolving 1.12 grams of the second metal catalyst precursor [$Co(NO_3)_2 \cdot 6H_2O$] in 15 mL of distilled water. Solution A and Solution B were then mixed together and added to the Beta-M50 zeolite support in the round bottom flask. The combined solution and the Beta-M50 zeolite support were mixed for 2 hours. The water was removed from the Beta-M50 zeolite support impregnated with the first and second metal catalyst precursors under vacuum at a temperature of 50° C., and the resulting hydrocracking catalyst precursor was dried overnight at a temperature of 100° C. The dried hydrocracking catalyst precursor was then calcined at a temperature of 500° C. for five hours to obtain the hydrocracking catalyst of Example 2.

Example 3: Transalkylation Catalyst Preparation

To prepare a transalkylation catalyst, the zeolites mordenite (with Si/Al ratio of 30) and ZSM-5 (with Si/Al ratio of 40) 5 grams each were separately disintegrated in two separate reaction flasks, using 0.40 M NaOH solution by gradual heating with stirring at 100° C. for 24 hours. The heating was carried out in the presence of a surfactant called cetyltrimethylammonium bromide (CTAB) (4.45%). The mixture was cooled down and then the pH was adjusted to 9.0 through the addition of 2N dilute sulfuric acid. The mixture was then stirred for 24 h and then aged at 100° C. for 24 hours to form meso-structured zeolites. The solid products were filtered, washed thoroughly using distilled water, dried at 80° C. overnight, then calcined at 550° C. for 6 hours to remove the surfactant. The composite material was then obtained was ion-exchanged 3 times with 0.05 M $NH_4NO_3$ solution at 80° C. for 5 hours. The resulting zeolites were mixed in 3:1 weight ratio of mesoporous mordenite and mesoporous ZSM-5. The composite mixture was combined with alumina binder (Cataloid AP-3, obtained from CCIC, Japan) to make extrudates by mixing 67 wt. % composite zeolite and 33 wt. % alumina binder and extruding the resulting mixture. These extrudates were loaded with 4 wt. % of molybdenum in the form of ammonium molybdate tetrahydrate through a wet impregnation technique and calcined at 400° C. for 5 hours to produce the transalkylation catalyst.

Example 4: Upgrading Pyrolysis Oil in the Presence of a Mixed Metal Oxide Catalyst, a Hydrocracking Catalyst, and a Transalkylation Catalyst In Example 4, the performance of the process including the mixed metal oxide catalyst of Example 1, the hydrocracking catalyst of Example 2, and the transalkylation catalyst of Example 3 for upgrading pyrolysis oil was evaluated. Raw pyrolysis oil from a stream cracker was mixed with toluene as a diluent to produce the pyrolysis oil feed. The toluene was added as a diluent to increase the fluidity of the pyrolysis oil feed so that the pyrolysis oil can better contact the mixed metal oxide catalyst surface. In particular, 16.74 g of pyrolysis oil was combined with 4.37 g of toluene to produce the pyrolysis oil feed. The resulting pyrolysis oil feed and 12.17 g of the mixed metal oxide catalyst of Example 1 were added to a first slurry reactor and mixed.

After adding the pyrolysis oil (with toluene) and mixed metal oxide catalyst to the first slurry reactor under atmospheric pressure and at room temperature, the first slurry reactor was sealed. The first slurry reactor was purged with pure hydrogen gas three times. The pressure was then increased to 140 bar (14 MPa) by introducing pure hydrogen gas at room temperature. The pyrolysis oil (with toluene) and mixed metal oxide catalyst were then heated to 400° C. and continuously stirred for four hours.

After the reaction, the first slurry reactor was cooled to room temperature. Then, the gas mixture was released and collected into a gas bag. The gas mixture was analyzed using gas chromatography. The reaction effluent was transferred to a separator (centrifuge). The reaction effluent was centrifuged at 10,000 revolutions per minute (rpm) for twenty minutes. Two layers were obtained after centrifuging, a top layer comprising the intermediate stream comprising mono-aromatic compounds, di-aromatic compounds, or both and a bottom layer comprising the used mixed metal oxide catalyst. The used mixed metal oxide catalyst was then washed with toluene to remove any condensate followed and vacuum dried. The used mixed metal oxide catalyst was vacuum dried at room temperature first and then at 100° C.

The intermediate stream was then added to a hydrocracking reactor with the speed of 0.6 g/hr. The hydrocracking catalyst was pretreated at the following conditions: from room temperature to 400° C., a heating rate of 5° C./min, and under $H_2$ flow rate of 25 ml/min and atmospheric pressure. The temperature of the hydrocracking catalyst was kept at 400° C. for 2 hours. The hydrocracking catalyst was pressured with $H_2$ until 30 bar and kept with $H_2$ flow rate of 25 ml/min. 0.5 g of pretreated hydrocracking catalyst was then added to the hydrocracking reactor. The intermediate stream was contacted with the hydrocracking catalyst for 24 hours at the hydrocracking reactor at the following reaction conditions, 400° C., $H_2$ flow rate of 25 ml/min, and 30 bar, to produce the hydrocracking effluent including aromatic compounds having six to nine carbon atoms.

The hydrocracking effluent was then added to a transalkylation reactor with the speed of 4.2 g/hr. The transalkylation catalyst was pretreated at the following conditions: from room temperature to 450° C., a heating rate of 5° C./min, and under $H_2$ flow rate of 50 ml/min and atmospheric pressure. The temperature of the transalkylation catalyst was kept at 450° C. for 2 hours. The transalkylation catalyst was pressured with $H_2$ until 20 bar and kept with $H_2$ flow rate of 50 ml/min. 1.0 g of pretreated transalkylation catalyst was then added to the transalkylation reactor. The hydrocracking effluent was reacted with the transalkylation catalyst for 1 to 48 hours at the transalkylation reactor at the following reaction conditions, 400° C., $H_2$ flow rate of 50 ml/min, and 20 bar, to produce the transalkylation effluent including xylenes.

Figure 3:
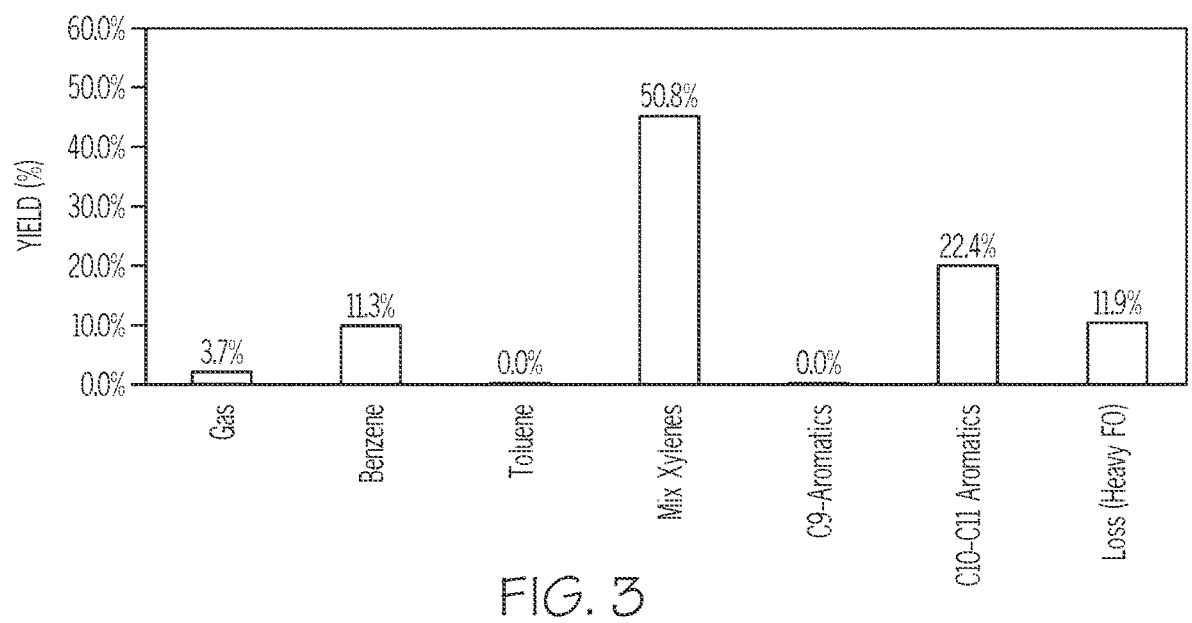
FIG. 3 graphically depicts weight percentage (y-axis) of various product effluent (x-axis) present in the transalkylation effluent produced from Example 4.

FIG. 3 provides the characteristics of the reaction effluent from the three stage reaction system. As shown in FIG. 3, after all three stages, the overall net yield of benzene, toluene, and xylenes was 61.2%. In FIG. 3, the net yield for toluene shown represents the amount of toluene produced by the reactions and does not include any contribution from the toluene added as a diluent. As further shown in FIG. 3, the after three stages, the overall net yield of xylenes was 50.8%.

Comparative Example 5: First Slurry Reactor Only

In Comparative Example 5, the performance of the mixed metal oxide catalyst of Example 1 alone for upgrading pyrolysis oil was evaluated. 16.74 g of pyrolysis oil and 12.17 g of the mixed metal oxide catalyst of Example 1 were added to a batch reactor and mixed. Before adding the pyrolysis oil, the pyrolysis oil was mixed with 4.37 g of toluene as a diluent to increase the fluidity of the pyrolysis oil such that the pyrolysis oil could have full contact with the surface of the mixed metal oxide catalyst.

After adding the pyrolysis oil (with toluene) and mixed metal oxide catalyst to the slurry reactor under atmospheric pressure and at room temperature, the batch reactor was sealed. The slurry reactor was purged with pure hydrogen gas three times. The pressure was then increased to 140 bar (14 MPa) by introducing pure hydrogen gas at room temperature. The pyrolysis oil (with toluene) and mixed metal oxide catalyst were then heated to 400° C. and continuously stirred for four hours.

After the reaction, the batch reactor was cooled to room temperature. Then, the gas mixture was released and collected into a gas bag. The gas mixture was analyzed using gas chromatography. The reaction effluent was transferred to a separator (centrifuge). The reaction effluent was centrifuged at 10,000 rpm for twenty minutes. Two layers were obtained after centrifuging, a top layer comprising the reaction product and a bottom layer comprising the used mixed metal oxide catalyst. The used mixed metal oxide catalyst was then washed with toluene to remove any condensate followed and vacuum dried. The used mixed metal oxide catalyst was vacuum dried at room temperature first and then at 100° C. The reaction product effluent was analyzed through simulated distillation (SIMDIS) gas chromatography, paraffins, isoparaffins, olefins, naphthenes, and aromatics (PIONA) gas chromatography, and high performance liquid chromatography (HPLC).

Table 1 provides the reaction conditions, characteristics of the pyrolysis oil, and characteristics of the reaction effluent.

TABLE 1

Reaction Conditions, Characteristics of Pyrolysis Oil, and Characteristics of Reaction Effluent

| Parameter | Value |
| --- | --- |
| Reaction Temperature (° C.) | 400 |
| Total Pressure Before Heating to Reaction Temperature (MPa) | 14 |
| Time on Stream (hours) | 4 |
| $C_{16}$ and $C_{16+}$ in Pyrolysis Oil (wt. %) | 41.3 |
| $C_{16}$ and $C_{16+}$ in Reaction Effluent (wt. %) | 0.5 |
| $C_{16}$ and $C_{16+}$ Conversion (%) | 98.8 |
| $H_2$ Conversion (%) | 33.5 |
| Gas Product Yield (wt. %) | 3.9 |
| Liquid Product Yield[1] (wt. %) | 96.1 |
| Mono-Aromatics ($C_6$-$C_9$) Yield (wt. %) | 41.3 |
| Di-Aromatics ($C_{10}$-$C_{13}$) Yield (wt. %) | 40.8 |
| Tri-Aromatics ($C_{14}$-$C_{16}$) Yield (wt. %) | 14.4 |
| Coke/Feed (%) | 0 |

[1]Toluene diluent was not considered as a product.

As shown in FIG. 3 and Table 1, Example 4 was more effective to convert the tetra-aromatics ($C_{16}$ and $C_{16+}$-hydrocarbons) in the pyrolysis oil to xylenes as compared to Comparative Example 5. While total mono-aromatic yield of Comparative Example 5 was 41.3 wt. %, total mono-aromatic yield of Example 4 was 62.1 wt. %. Further, the xylene yield of Example 4 was 50.8 wt. %, which is substantially greater than the total mono-aromatic yield of Comparative Example 5 (41.3 wt. %).

A first aspect of the present disclosure may be directed to a method for upgrading pyrolysis oil. The method may include contacting the pyrolysis oil feed with hydrogen in the presence of a mixed metal oxide catalyst in a slurry reactor to produce light aromatic compounds. The pyrolysis oil feed may comprise multi-ring aromatic compounds comprising greater than or equal to sixteen carbon atoms. The mixed metal oxide catalyst may comprise a plurality of catalyst particles, and each of the plurality of catalyst particles may comprise a plurality of different metal oxides. The method may further include contacting the pyrolysis oil feed with hydrogen in the presence of the mixed metal oxide catalyst in the slurry reactor to convert at least a portion of the multi-ring aromatic compounds in the pyrolysis oil feed to the light aromatic compounds comprising mono-aromatic compounds, di-aromatic compounds, or both. The method may further include passing an intermediate stream comprising the light aromatic compounds from the slurry reactor to a hydrocracking reactor, and contacting the intermediate stream with hydrogen in the presence of a hydrocracking catalyst in the hydrocracking reactor. The contacting may cause at least a portion of the light aromatic compounds in the intermediate stream to undergo hydrocracking to produce a hydrocracking effluent comprising aromatic compounds having six to nine carbon atoms. The method may further include passing the hydrocracking effluent from the hydrocracking reactor to a transalkylation reactor, and contacting the hydrocracking effluent with hydrogen in the presence of a transalkylation catalyst in the transalkylation reactor. The contacting may cause at least a portion of the aromatic compounds in the hydrocracking effluent to undergo transalkylation to produce a transalkylation effluent comprising xylenes.

A second aspect of the present disclosure may include the first aspect, in which the transalkylation effluent may comprise a concentration of xylenes greater than a concentration of xylenes in the pyrolysis oil, the intermediate stream, the hydrocracking effluent, or combinations of these.

A third aspect of the present disclosure may include either one of the first or second aspects, in which the aromatic compounds having six to nine carbon atoms may comprise benzene, toluene, ethyl-benzene, xylenes, or combinations thereof.

A fourth aspect of the present disclosure may include any one of the first through third aspects, in which the pyrolysis oil feed may comprise greater than or equal to 30 weight percent (wt. %) multi-ring aromatic compounds having greater than or equal to sixteen carbon atoms based on the total weight of the pyrolysis oil in the pyrolysis oil.

A fifth aspect of the present disclosure may include any one of the first through fourth aspects, comprising contacting the pyrolysis oil feed with hydrogen in the presence of the mixed metal oxide catalyst in the slurry reactor at one or more of the following reaction conditions: (a) a temperature of from 350 degrees Celsius (° C.) to 500° C.; (b) a pressure of from 1 megapascal (MPa) (10 bar) to 5 MPa (50 bar); (c) a volume ratio of hydrogen to the pyrolysis oil of from 500 to 3000; (d) weight hourly space velocity (WHSV) of from 0.5 per hours ($h^{-1}$) to 2.0 $h^{-1}$, or combinations of any of these reaction conditions (a)-(d).

A sixth aspect of the present disclosure may include any one of the first through fifth aspects, in which the first metal oxide and the second metal oxide may each comprise oxides of metals in groups 3-13 of the International Union of Pure and Applied Chemistry (IUPAC) periodic table.

A seventh aspect of the present disclosure may include any one of the first through sixth aspects, in which the mixed metal oxide catalyst may consist of the first metal oxide and the second metal oxide, where each of the first metal oxide and the second metal oxide may comprise oxides of one or more metals selected from the group consisting of iron, zirconium, cerium, aluminum, tungsten, molybdenum, titanium, and combinations of these, and where the second metal oxide is different from the first metal oxide.

An eighth aspect of the present disclosure may include any one of the first through seventh aspects, in which the first metal oxide and the second metal oxide may each comprise oxides of one or more metals selected from the group consisting of iron, zirconium, cerium, aluminum, tungsten, molybdenum, titanium, and combinations of these, where the second metal oxide is different from the first metal oxide.

A ninth aspect of the present disclosure may include any one of the first through eighth aspects, in which the mixed metal oxide catalyst may comprise: from 60 wt. % to 95 wt. % iron oxide; from 1 wt. % to 20 wt. % zirconium oxide; from 0.1 wt. % to 10 wt. % cerium oxide; and from 1 wt. % to 20 wt. % aluminum oxide, where the weight percentages are based on the total weight of the mixed metal oxide catalyst.

A tenth aspect of the present disclosure may include any one of the first through ninth aspects, in which contacting the pyrolysis oil feed with hydrogen in the presence of the mixed metal oxide catalyst in the slurry reactor may convert the portion of the multi-ring aromatic compounds in the pyrolysis oil to the light aromatic compounds in a single step, without conducting a subsequent chemical reaction step.

An eleventh aspect of the present disclosure may include any one of the first through tenth aspects, further comprising mixing the pyrolysis oil feed with toluene upstream of the slurry reactor to produce a dilute pyrolysis oil feed and passing the dilute pyrolysis oil feed to the slurry reactor.

A twelfth aspect of the present disclosure may include any one of the first through eleventh aspects, comprising mixing the pyrolysis oil and a diluent to produce the pyrolysis oil feed having an amount of diluent of from 10 wt. % to 90 wt. %, or from 60 wt. % to 80 wt. % based on the total weight of the pyrolysis oil feed.

A thirteenth aspect of the present disclosure may include any one of the first through twelfth aspects, further comprising separating a slurry reactor effluent from the slurry reactor to produce used mixed metal oxide catalyst and the intermediate stream.

A fourteenth aspect of the present disclosure may include any one of the first through thirteenth aspects, further comprising passing the slurry reactor effluent to the slurry reactor effluent separator operable to separate the slurry reactor effluent to produce the used mixed metal oxide catalyst and the intermediate stream.

A fifteenth aspect of the present disclosure may include any one of the first through fourteenth aspects, further comprising recycling the used mixed metal oxide catalyst back to the slurry reactor.

A sixteenth aspect of the present disclosure may include any one of the first through fifteenth aspects, comprising passing the intermediate stream directly from the slurry reactor effluent separator to the hydrocracking reactor.

A seventeenth aspect of the present disclosure may include any one of the first through sixteenth aspects, comprising contacting the intermediate stream with hydrogen in the presence of the hydrocracking catalyst at one or more of the following reaction conditions: (a) a temperature of from 350° C. to 500° C.; (b) a pressure of from 1 MPa (10 bar) to 5 MPa (50 bar); (c) a volume ratio of hydrogen to the light aromatic compounds of from 500 to 3000; (d) WHSV of 0.5 $h^{-1}$ to 2.0 $h^{-1}$, or combinations of any of these reaction conditions (a)-(d).

An eighteenth aspect of the present disclosure may include any one of the first through seventeenth aspects, in which the hydrocracking catalyst may comprise the mesoporous zeolite supported metal catalyst comprising a mesoporous zeolite support and at least one of a first metal catalyst and a second metal catalyst deposited on outer surfaces and pore surfaces of the mesoporous zeolite support.

A nineteenth aspect of the present disclosure may include any one of the first through eighteenth aspects, in which at least one of the first metal catalyst and the second metal catalyst may comprise a heteropolyacid.

A twentieth aspect of the present disclosure may include any one of the first through nineteenth aspects, in which the heteropolyacid may comprise: at least one metal selected from cobalt, molybdenum, vanadium, or combinations of these; and at least one heteroatom selected from phosphorous, silicon, arsenic, or combinations of these.

A twenty-first aspect of the present disclosure may include any one of the first through twentieth aspects, in which the first metal catalyst may comprise a first heteropolyacid and the second metal catalyst comprises a second heteropolyacid that is different from the first heteropolyacid.

A twenty-second aspect of the present disclosure may include any one of the first through twenty-first aspects, in which the heteropolyacid may comprise a Keggin structure having general formula $XM_{12}O_{40}{}^{n-}$ or a Dawson structure having the general formula $XM_{18}O_{82}{}^{n-}$, in which X is the heteroatom; M is molybdenum and optionally one or more of cobalt, vanadium, or a combination of these; and n− is an integer indicative of the charge of the anion of the heteropolyacid.

A twenty-third aspect of the present disclosure may include any one of the first through twenty-second aspects, in which the heteropolyacid may comprise phosphormolybdic heteropolyacid having formula $H_3PMo_{12}O_{40}$, decamolybdodicobaltate heteropolyacid having chemical formula $H_6[Co_2Mo_{10}O_{38}H_4]$, or silicomolybdic heterpolyacid having chemical formula $H_4[SiMo_{12}O_{40}]$.

A twenty-fourth aspect of the present disclosure may include any one of the first through twenty-third aspects, in which the mesoporous zeolite support may have an average pore size of from 2 nanometers (nm) to 40 nm as determined by Barrett-Joyner-Halenda (BJH) analysis.

A twenty-fifth aspect of the present disclosure may include any one of the first through twenty-fourth aspects, in which the zeolite support may comprise a molar ratio of silica to alumina of from 10 to 70.

A twenty-sixth aspect of the present disclosure may include any one of the first through twenty-fifth aspects, in which contacting the intermediate stream with hydrogen in the presence of the hydrocracking catalyst in the hydrocracking reactor may convert the portion of the light aromatic compounds to the hydrocracking effluent in a single step, without conducting a subsequent chemical reaction step.

A twenty-seventh aspect of the present disclosure may include any one of the first through twenty-sixth aspects, comprising passing the hydrocracking effluent directly from the hydrocracking reactor to the transalkylation reactor.

A twenty-eighth aspect of the present disclosure may include any one of the first through twenty-seventh aspects, comprising contacting the hydrocracking effluent with hydrogen in the presence of the transalkylation catalyst at one or more of the following reaction conditions: (a) a temperature of from 350° C. to 500° C.; (b) a pressure of from 1 MPa (10 bar) to 5 MPa (50 bar); (c) a volume ratio of hydrogen to the hydrocracking effluent of from 500 to 1500; (d) WHSV of from $0.5\ h^{-1}$ to $5.0\ h^{-1}$, or combinations of any of these reaction conditions (a)-(d).

A twenty-ninth aspect of the present disclosure may include any one of the first through twenty-eighth aspects, in which the transalkylation catalyst may comprise a solid zeolite composite and a metal.

A thirtieth aspect of the present disclosure may include any one of the first through twenty-ninth aspects, in which the solid zeolite composite may comprise mesoporous mordenite zeolite and mesoporous ZSM-5 in a 1:1 to 5:1 weight ratio.

A thirty-first aspect of the present disclosure may include any one of the first through thirtieth aspects, in which the transalkylation catalyst may have a mesostructure comprising at least one disordered mesophase and at least one ordered mesophase.

A thirty-second aspect of the present disclosure may include any one of the first through thirty-first aspects, in which the transalkylation catalyst may comprise the metal comprising molybdenum, platinum, rhenium, nickel, or combinations thereof.

A thirty-third aspect of the present disclosure may include any one of the first through thirty-second aspects, in which contacting the hydrocracking effluent with hydrogen in the presence of the transalkylation catalyst at the third reaction condition may convert the portion of the hydrocracking effluent to the transalkylation effluent in a single step, without conducting a subsequent chemical reaction step.

A thirty-fourth aspect of the present disclosure may include any one of the first through thirty-third aspects, in which contacting the pyrolysis oil with hydrogen in the presence of the mixed metal oxide catalyst, contacting the light aromatic compounds with hydrogen in the presence of the hydrocracking catalyst, and contacting the hydrocracking effluent with hydrogen in the presence of the transalkylation catalyst may result in a yield of greater than or equal to 50 wt. % of xylene based on the total weight of pyrolysis oil in the pyrolysis oil feed.

A thirty-fifth aspect of the present disclosure may include any one of the first through thirty-fourth aspects, further comprising separating the transalkylation effluent in a transalkylation effluent separator to produce a light gas effluent, a xylene-containing effluent, and a transalkylation bottom stream.

A thirty-sixth aspect of the present disclosure may include any one of the first through thirty-fifth aspects, further comprising recycling the transalkylation bottom stream from the transalkylation effluent separator back to the hydrocracking reactor.

A thirty-seventh aspect of the present disclosure may be directed to a system for upgrading pyrolysis oil. The system may include a slurry reactor comprising a mixed metal oxide catalyst comprising a plurality of catalyst particles. Each of the plurality of catalyst particles may comprise a plurality of different metal oxides. The slurry reactor may be operable to contact the pyrolysis oil feed with hydrogen in the presence of the mixed metal oxide catalyst to produce light aromatic compounds comprising mono-aromatic compounds, di-aromatic compounds, or both. The system may further include a slurry reactor effluent separator disposed downstream of the slurry reactor and operable to separate the slurry reactor effluent to produce a used mixed metal oxide catalyst and an intermediate stream comprising the light aromatic compounds. The system may further include a hydrocracking reactor disposed downstream of the slurry reactor effluent separator and comprising a hydrocracking catalyst. The hydrocracking reactor may be operable to contact the intermediate stream with hydrogen in the presence of the hydrocracking catalyst to produce a hydrocracking effluent comprising aromatic compounds having six to nine carbon atoms. The system may further include a transalkylation reactor disposed downstream of the hydrocracking reactor and comprising a transalkylation catalyst. The transalkylation reactor may be operable to contact the hydrocracking effluent with hydrogen in the presence of the transalkylation catalyst to produce a transalkylation effluent comprising xylenes.

A thirty-eighth aspect of the present disclosure may include the thirty-seventh aspect, in which the hydrocracking reactor, the transalkylation reactor or both may be fixed bed reactors.

A thirty-ninth aspect of the present disclosure may include either the thirty-seventh or thirty-eighth aspect, in which the transalkylation effluent may comprise a concentration of xylenes greater than a concentration of xylenes in the pyrolysis oil, the intermediate stream, the hydrocracking effluent, or combinations of these.

A fortieth aspect of the present disclosure may include any one of the thirty-seventh through thirty-ninth aspects, in which the slurry reactor may be operable to contact the pyrolysis oil with hydrogen in the presence of the mixed metal oxide catalyst at one or more of the following reaction conditions: (a) a temperature of from 350° C. to 500° C.; (b) a pressure of from 1 MPa (10 bar) to 5 MPa (50 bar); (c) a volume ratio of hydrogen to the pyrolysis oil of from 500 to 3000; (d) WHSV of from $0.5\ h^{-1}$ to $2.0\ h^{-1}$, or combinations of these reaction conditions (a)-(d).

A forty-first aspect of the present disclosure may include any one of the thirty-seventh through fortieth aspects, in which the hydrocracking reactor may be operable to contact the light aromatic compounds with hydrogen in the presence of the hydrocracking catalyst at one or more of the following reaction conditions: (a) a temperature of from 350° C. to 500° C.; (b) a pressure of from 1 MPa (10 bar) to 5 MPa (50 bar); (c) a volume ratio of hydrogen to the light aromatic compounds of from 500 to 3000; (d) WHSV of from 0.5 h$^{-1}$ to 2.0 h$^{-1}$, or combinations of these reaction conditions (a)-(d).

A forty-second aspect of the present disclosure may include any one of the thirty-seventh through forty-first aspects, in which the transalkylation reactor may be operable to contact the hydrocracking effluent with hydrogen in the presence of the transalkylation catalyst at one or more of the following reaction conditions: (a) a temperature of from 350° C. to 500° C.; (b) a pressure of from 1 MPa (10 bar) to 5 MPa (50 bar); (c) a volume ratio of hydrogen to the hydrocracking effluent of from 500 to 1500; (d) WHSV of from 0.5 h$^{-1}$ to 5.0 h$^{-1}$, or combinations of these reaction conditions (a)-(d).

A forty-third aspect of the present disclosure may include any one of the thirty-seventh through forty-second aspects, in which the slurry reactor effluent separator may be directly downstream of the slurry reactor.

A forty-fourth aspect of the present disclosure may include any one of the thirty-seventh through forty-third aspects, in which the hydrocracking reactor may be directly downstream of the slurry reactor effluent separator.

A forty-fifth aspect of the present disclosure may include any one of the thirty-seventh through forty-fourth aspects, in which the transalkylation reactor may be directly downstream of the hydrocracking reactor.

A forty-sixth aspect of the present disclosure may include any one of the thirty-seventh through forty-fifth aspects, in which the hydrocracking catalyst may comprise the mesoporous zeolite supported metal catalyst comprising a mesoporous zeolite support and at least one of a first metal catalyst and a second metal catalyst deposited on outer surfaces and pore surfaces of the mesoporous zeolite support.

A forty-seventh aspect of the present disclosure may include any one of the thirty-seventh through forty-sixth aspects, in which the transalkylation catalyst may comprise a solid zeolite composite and a metal.

A forty-eighth aspect of the present disclosure may include any one of the thirty-seventh through forty-seventh aspects, further comprising the transalkylation effluent separator directly downstream of the transalkylation reactor and operable to separate the transalkylation effluent to a light gas effluent, a xylene-containing effluent, and a transalkylation bottom stream.

A forty-ninth aspect of the present disclosure may include any one of the thirty-seventh through forty-eighth aspects, in which the transalkylation bottom stream may be recycled back to the hydrocracking reactor.

A fiftieth aspect of the present disclosure may include any one of the thirty-seventh through forty-ninth aspects, where the used mixed metal oxide catalyst may be recycled back to the slurry reactor.

As used in the Specification and appended claims, the singular forms "a", "an", and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced. For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter. The transitional phrases "consisting of" and "consisting essentially of" may be interpreted to be subsets of the open-ended transitional phrases, such as "comprising" and "including," such that any use of an open-ended phrase to introduce a recitation of a series of elements, components, materials, or steps should be interpreted to also disclose a recitation of the series of elements, components, materials, or steps using the closed terms "consisting of" and "consisting essentially of." For example, the recitation of a composition "comprising" components A, B, and C should be interpreted as also disclosing a composition "consisting of" components A, B, and C as well as a composition "consisting essentially of" components A, B, and C. Any quantitative value expressed in the present application may be considered to include open-ended embodiments consistent with the transitional phrases "comprising" or "including" as well as closed or partially closed embodiments consistent with the transitional phrases "consisting of" and "consisting essentially of."

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A method for upgrading pyrolysis oil, the method comprising:
   contacting the pyrolysis oil feed with hydrogen in the presence of a mixed metal oxide catalyst in a slurry reactor to produce light aromatic compounds, where:
   the pyrolysis oil feed comprises multi-ring aromatic compounds comprising greater than or equal to sixteen carbon atoms;

the mixed metal oxide catalyst comprises a plurality of catalyst particles and each of the plurality of catalyst particles comprises a plurality of different metal oxides; and contacting the pyrolysis oil feed with hydrogen in the presence of the mixed metal oxide catalyst in the slurry reactor to convert at least a portion of the multi-ring aromatic compounds in the pyrolysis oil feed to the light aromatic compounds comprising mono-aromatic compounds, di-aromatic compounds, or both;

passing an intermediate stream comprising the light aromatic compounds from the slurry reactor to a hydrocracking reactor;

contacting the intermediate stream with hydrogen in the presence of a hydrocracking catalyst in the hydrocracking reactor, where:

the contacting causes at least a portion of the light aromatic compounds in the intermediate stream to undergo hydrocracking to produce a hydrocracking effluent comprising aromatic compounds having six to nine carbon atoms; and the hydrocracking catalyst comprises a mesoporous zeolite supported metal catalyst comprising a mesoporous zeolite support and at least one of a first metal catalyst and a second metal catalyst deposited on outer surfaces and pore surfaces of the mesoporous zeolite support;

passing the hydrocracking effluent from the hydrocracking reactor to a transalkylation reactor; and contacting the hydrocracking effluent with hydrogen in the presence of a transalkylation catalyst in the transalkylation reactor, where the contacting causes at least a portion of the aromatic compounds in the hydrocracking effluent to undergo transalkylation to produce a transalkylation effluent comprising xylenes.

2. The method of claim 1, in which the transalkylation effluent comprises a concentration of xylenes greater than a concentration of xylenes in the pyrolysis oil, the intermediate stream, the hydrocracking effluent, or combinations of these.

3. The method of claim 1, in which the aromatic compounds having six to nine carbon atoms comprise benzene, toluene, ethyl-benzene, xylenes, or combinations thereof.

4. The method of claim 1, in which the pyrolysis oil feed comprises greater than or equal to 30 weight percent (wt. %) multi-ring aromatic compounds having greater than or equal to sixteen carbon atoms based on the total weight of the pyrolysis oil in the pyrolysis oil.

5. The method of claim 1, comprising contacting the pyrolysis oil feed with hydrogen in the presence of the mixed metal oxide catalyst in the slurry reactor at one or more of the following reaction conditions: (a) a temperature of from 350 degrees Celsius (° C.) to 500° C.; (b) a pressure of from 1 megapascal (MPa) (10 bar) to 5 MPa (50 bar); (c) a volume ratio of hydrogen to the pyrolysis oil of from 500 to 3000; (d) weight hourly space velocity (WHSV) of from 0.5 per hours ($h^{-1}$) to 2.0 $h^{-1}$, or combinations of these reaction conditions.

6. The method of claim 1, in which the mixed metal oxide catalyst comprises a first metal oxide and a second metal oxide different from the first metal oxide, where each of the first metal oxide and the second metal oxide comprises oxides of metals in groups 3-13 of the International Union of Pure and Applied Chemistry (IUPAC) periodic table.

7. The method of claim 1, in which the mixed metal oxide catalyst consists of a first metal oxide and a second metal oxide different from the first metal oxide, where each of the first metal oxide and the second metal oxide comprising oxides of one or more metals selected from the group consisting of iron, zirconium, cerium, aluminum, tungsten, molybdenum, titanium, and combinations of these.

8. The method of claim 7, in which the mixed metal oxide catalyst comprises:
from 60 wt. % to 95 wt. % iron oxide;
from 1 wt. % to 20 wt. % zirconium oxide;
from 0.1 wt. % to 10 wt. % cerium oxide; and
from 1 wt. % to 20 wt. % aluminum oxide,
where the weight percentages are based on the total weight of the mixed metal oxide catalyst.

9. The method of claim 1, further comprising mixing the pyrolysis oil feed with toluene upstream of the slurry reactor to produce a dilute pyrolysis oil feed and passing the dilute pyrolysis oil feed to the slurry reactor.

10. The method of claim 1, further comprising separating a slurry reactor effluent from the slurry reactor to produce used mixed metal oxide catalyst and the intermediate stream, and recycling the used mixed metal oxide catalyst back to the slurry reactor.

11. The method of claim 1, comprising contacting the intermediate stream with hydrogen in the presence of the hydrocracking catalyst at one or more of the following reaction conditions: (a) a temperature of from 350° C. to 500° C.; (b) a pressure of from 1 MPa (10 bar) to 5 MPa (50 bar); (c) a volume ratio of hydrogen to the light aromatic compounds of from 500 to 3000; (d) WHSV of from 0.5 $h^{-1}$ to 2.0 $h^{-1}$, or combinations of these reaction conditions.

12. The method of claim 1, in which at least one of the first metal catalyst and the second metal catalyst comprises a heteropolyacid, where the heteropolyacid comprises:
at least one metal selected from cobalt, molybdenum, vanadium, or combinations of these; and
at least one heteroatom selected from phosphorous, silicon, arsenic, or combinations of these.

13. The method of claim 1, comprising passing the hydrocracking effluent directly from the hydrocracking reactor to the transalkylation reactor.

14. The method of claim 1, comprising contacting the hydrocracking effluent with hydrogen in the presence of the transalkylation catalyst at one or more of the following reaction conditions: (a) a temperature of from 350° C. to 500° C.; (b) a pressure of from 1 MPa (10 bar) to 5 MPa (50 bar); (c) a volume ratio of hydrogen to the hydrocracking effluent of from 500 to 1500; (d) WHSV of from 0.5 $h^{-1}$ to 5.0 $h^{-1}$, or combinations of these reaction conditions.

15. The method of claim 1, in which the transalkylation catalyst comprises a solid zeolite composite and a metal.

16. The method of claim 15, in which the solid zeolite composite comprises a large pore mesoporous mordenite zeolite and a medium pore mesoporous ZSM-5 zeolite in a 1:1 to 5:1 weight ratio.

17. The method of claim 1, in which contacting the pyrolysis oil with hydrogen in the presence of the mixed metal oxide catalyst, contacting the light aromatic compounds with hydrogen in the presence of the hydrocracking catalyst, and contacting the hydrocracking effluent with hydrogen in the presence of the transalkylation catalyst result in a yield of greater than or equal to 50 wt. % of xylene based on the total weight of pyrolysis oil in the pyrolysis oil feed.

* * * * *